(12) United States Patent
Meier et al.

(10) Patent No.: US 10,131,685 B2
(45) Date of Patent: Nov. 20, 2018

(54) DI- AND TRIPHOSPHATE PRODRUGS

(71) Applicant: Universitaet Hamburg, Hamburg (DE)

(72) Inventors: Chris Meier, Jork (DE); Tristan Gollnest, Ahrensburg (DE); Tobias Nack, Hamburg (DE); Lina Weinschenk, Hamburg (DE)

(73) Assignee: Universitaet Hamburg, Hamburg (DE)

( * ) Notice: Subject to any disclaimer, the term of this patent is extended or adjusted under 35 U.S.C. 154(b) by 0 days.

(21) Appl. No.: 15/505,281

(22) PCT Filed: Aug. 17, 2015

(86) PCT No.: PCT/DE2015/200440
§ 371 (c)(1),
(2) Date: Feb. 21, 2017

(87) PCT Pub. No.: WO2016/026493
PCT Pub. Date: Feb. 25, 2016

(65) Prior Publication Data
US 2017/0275328 A1 Sep. 28, 2017

(30) Foreign Application Priority Data
Aug. 22, 2014 (DE) ........................ 10 2014 112 055

(51) Int. Cl.
C07H 19/10 (2006.01)
C07F 9/6558 (2006.01)
A01N 43/04 (2006.01)
A61K 31/70 (2006.01)

(52) U.S. Cl.
CPC ......... *C07H 19/10* (2013.01); *C07F 9/65586* (2013.01)

(58) Field of Classification Search
None
See application file for complete search history.

(56) References Cited

FOREIGN PATENT DOCUMENTS

WO 2009129798 A2 10/2009

OTHER PUBLICATIONS

International Preliminary Report on Patentability dated Mar. 9, 2017, in International Application No. PCT/DE2015/200440.
Jessen, Henning Jacob et al. "Bioreversible Protection of Nucleoside Diphosphates" Angewandte Chemie, Int. Ed. 2008, vol. 47, pp. 8719-8722 Wiley-VCH Verlag GmbH & Co. KGaA, Weinheim, Germany www.angewandte.org, DOI: 10.1002/anie.200803100.
Schulz, Tilmann "Synthese und Untersuchung von Nucleosiddisphosphat Prodrugs" Dissertation submitted to the Department of Chemistry, University of Hamburg, Hamburg, Germany, 2011 English Abstract.
Pertusati, Fabrizio et al "Medicinal Chemistry of Nucleoside Phosphonate Prodrugs for antiviral therapy" Welsh School of Pharmacy, Cardiff University, Cardiff, UK Antiviral Chemistry & Chemotherapy, 2012, vol. 22, pp. 181-203 (doi:10.3851/IMP2012).
Schulz, Tilmann et al. "The DiPPro Approach: Synthesis, Hydrolysis, and Antiviral Activity of Lipophilic d4T Diphosphate Prodrugs" ChemMedChem 2014, vol. 9, pp. 762-775, DOI: 10.1002/cmdc.201300500 Wiley Online Library, 2014 Wiley-VCH Verlag GmbH & Co. KGaA, Weinheim, Germany.
Gollnest, Tristan et al. "The Tripppro-Approach: Development of Nucleoside Triphosphate Prodrugs" "Synthesis and Characterization of Biologically Active Nucleoside Triphosphate Prodrugs" Abstract and Poster presented on 27th International Conference on Antiviral Research (ICAR), May 12-16, 2014, Raleigh,North Carolina, USA.
Nack, Tobias et al. "Synthesis and Investigation of Potential Anti-HIV Active Nucleoside Triphosphate Prodrugs (TriPPPro-Compounds) Synthesis and Investigation of Potential Anti-HIV Active Nucleoside Triphosphate (NTP) Prodrugs" Abstract and Poster presented on 27th International Conference on Antiviral Research (ICAR), May 12-16, 2014, Raleigh, North Carolina, USA.
Weinschenk, Lina et al. "The Dippro Approach: New Insights in Diphosphate Prodrugs" Poster, presented on 21st International Round Table on Nucleosides, Nucleotides and Nucleic Acids (IS3NA), Aug. 24-28, 2014, Poznań, Poland.
International Search Report and Written Opinion dated Dec. 10, 2015, in International Application No. PCT/DE2015/200440.
Meier, Chris et al. "Nucleoside Diphosphate Prodrugs" Organic Chemistry, Department of Chemistry, University of Hamburg, Germany, Rega Institute for Medical Research, Katholieke University of Leuven, Belgium Oxford University Press, Symposium date: Sep. 8, 2008, Nucleic Acids Symposium Series No. 52, pp. 83-84.
Nack, Tobias et al. "Synthesis and Investigation of Potential Anti-HIV active nucleoside triphosphate (NTP) Prodrugs" Organic Chemistry, Department of Chemistry, University of Hamburg, Germany, Rega Institute for Medical Research, Katholieke University of Leuven, Belgium Program and Abstract of the 27th International Conference on Antiviral Research (ICAR), Raleigh, NC May 2014.
Lam, Angela et al. "Hepatitis C Virus Nucleotide Inhibitors PSI-352938 and PSI-353661 Exhibit a Novel Mechanism of Resistance Requiring Multiple Mutations within Replicon RNA" Pharmasset, Inc., 303A College Road East, Princeton, New Jersey 08540 Journal of Virology, Dec. 2011, pp. 12334-12342, vol. 85, No. 23.

(Continued)

*Primary Examiner* — Patrick T Lewis
(74) *Attorney, Agent, or Firm* — Stephan A. Pendorf; Patent Central LLC

(57) ABSTRACT

Compounds which can be used as prodrugs, in particular nucleoside diphosphate and triphosphate prodrugs, and a method for producing these compounds. The aim is to provide improved di- and/or triphosphate prodrugs, in particular nucleotide or nucleotide analog prodrugs. This is achieved in one aspect by providing bioreversibly and asymmetrically masked di- and triphosphate compounds, in particular nucleoside diphosphate and nucleoside triphosphate compounds or the analogs thereof. The masking only occurs at the terminal phosphate, i.e. at the β- or γ-phosphate, whereas the masking of the internal phosphate is omitted.

13 Claims, 1 Drawing Sheet

(56) References Cited

OTHER PUBLICATIONS

Sureshan, Kana M. et al. Rapid and efficient routes to phosphatidylinositolo 3,4,5-triphosphates via myo-inositol orthobenzoate Wolfson Laboratory of Medicinal Chemistry, Department of Pharmacy and Pharmacology, University of Bath, UK Tetrahedron Letters 48 (2007), pp. 1923-1926, Elsevier Ltd.

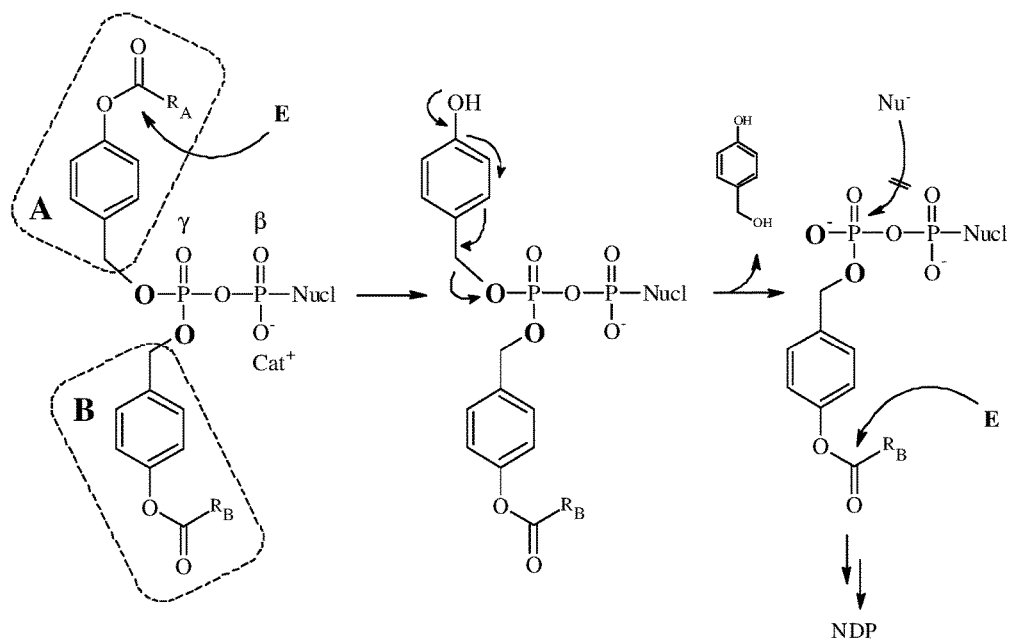

DI- AND TRIPHOSPHATE PRODRUGS

The invention relates to compounds that can be used as prodrugs, in particular nucleoside di- and triphosphate prodrugs, and a method for producing said compounds.

Nucleoside analogues which can be incorporated in DNA are used in the treatment of infectious viral diseases such as herpes or hepatitis infections or the immunodeficiency disease AIDS (Acquired Immunodeficiency Syndrome), for example, but also to combat cancer. Once they are incorporated in the DNA, the nucleoside analogues often function as chain terminators, that is to say no further elongation takes place in the 3' direction (J. Balzarini, P. Herdewijn, E. De Clercq; Differential Patterns of intracellular Metabolism of 2',3'-Didehydro-2',3'-dideoxythymidine and 3'-Azido-2',3'-dideoxythymidine, two potent Anti-human Immunodeficiency Virus Compounds; J. Biol. Chem. 1989, 264, 6127-6133). However, the nucleoside analogues must be present in the form of triphosphates (NTP) before they can be incorporated in the DNA strand to extend the chain.

In mono-, di- or triphosphate (NMP, NDP, NTP) forms thereof, nucleoside analogues are unable to penetrate the cell membrane under physiological conditions because of their charge. It is also impossible for them to pass through the blood brain barrier (BBB) to treat diseases which also affect the brain. Therefore, nucleoside analogues must either be converted into the triphosphates thereof in several stages by certain more or less specific kinases when they are already in the cell, or they must be arranged or modified so that they can pass through the cell membrane and/or the BBB.

In order to do this, typically the lipophilicity of the medications must be increased (e.g., R. J. Sawchuk, Z. Yang; Investigation of distribution, transport and uptake of anti-HIV drugs to the central nervous system; Advanced Drug Delivery Reviews 1999, 39, 5-31). One possible way to increase the lipophilicity of known medications may be seen in the use of prodrug systems. Prodrugs are active substance precursors which ideally do not release the actual active substance until it reaches the desired target site by cleaving masking groups. Besides increased lipophilicity, such prodrugs must also satisfy requirements such as sufficient stability in the extracellular medium and the masks they release must be non-toxic.

Enzymatically activatable prodrug systems for nucleoside monophosphates (NMP) have already been described (A. Pompon, I. Lefebvre, J.-L. Imbach, S. Khan, D. Farquhar; Decomposition Pathways of the Mono-(Pivaloyloxymethyl) and Bis-(Pivaloyloxymethyl) Esters of Azidothymidine-5'-Monophosphate in Cell Extract and in Tissue-Culture Medium—An Application of the Online Isrp-Cleaning HPLC Technique; Antiviral Chem. Chemother. 1994, 5, 91-98; I. Lefebvre, C. Perigaud, A. Pompon, A.-M. Aubertin, J.-L. Girardet, A. Kim, G. Gosselin, J.-L. Imbach; Mononucleoside Phosphotriester Derivates with S Acyl-2-thioethyl Bioreversible Phosphate-Protecting Groups: Intracellular Delivery of 3'-Azido-2',3'-dideoxythymidine-5'-monophosphate; J. Med. Chem. 1995, 38, 3941-3950; W. Thomson, D. Nicholls, W. J. Irwin, J. S. Al-Mushadani, S. Freeman, A. Karpas, J. Petrik, N. Mahmood, A. J. Hay; Synthesis, Bioactivation and Anti-HIV Activity of the Bis (4-acyloxybenzyl) and Mono(4-acyloxybenzyl) Esters of the 5'-Monophosphate of AZT, J. Chem. Soc., Perkin Trans., 1993, 1, 1239-1245; Thomson, D. Nicholls, W. J. Irwin, J. S. Al-Mushadani, S. Freeman, A. Karpas, J. Petrik, N. Mahmood, A. J. Hay, Synthesis, Bioactivation and Anti-HIV Activity of the Bis(4-acyloxybenzyl) and Mono(4-acyloxybenzyl) Esters of the 5'-Monophosphate of AZT, J. Chem. Soc., Perkin Trans., 1993, 1, 1239-1245; A. Routledge, I. Walker, S. Freeman, A. Hay, N. Mahmood, Synthesis, Bioactivation and Anti-HIV Activity of 4-Acyloxybenzyl Bis(Nucleosid-5-yl) Phosphates; Nucl. Nucl., 1995, 14, 1545-1558; C. Meier, CycloSal Phosphates as Chemical trojan Horses for the intracellular Nucleotide and Glycosylmonophosphate Delivery—Chemistry meets Biology, European Journal of Organic Chemistry 2006, 1081-1102). However, a drawback in the use of NMP prodrugs is that their essential subsequent phosphorylisation to form the di- and triphosphates in the cell can be inhibited or entirely prevented. Thus for example, in the case of the nucleoside analogue azidothymidine (AZT), a known anti-HIV medication, phosphorylisation to form AZTDP (DP=diphosphate) is inhibited. Moreover, many side effects are ascribed to the corresponding monophosphate AZTMP (MP=monophosphate).

There is still no satisfactory solution for masking nucleosidediphosphates (NDP) and nucleosidetriphosphates (NTP). The difficulty in these cases is that, unlike NMP, there is not just one phosphate group present, but one or two energy-rich phosphoric acid anhydride bond(s), which has/have to be masked reversibly in the form of the pyrophosphate unit without breaking the anhydride bond(s). A reaction must not ensue on the phosphorus atom when the pyrophosphate unit is demasked, as this can lead to a break in the pyrophosphate bridge. This essentially differentiates NDP- and NTP prodrugs form their NMP relatives. Hydrolysis reactions can also take place on the phosphorus atom.

Symmetrically masked nucleoside di- and -triphosphates and a production method therefor are described in WO 2009/129798 A2. In this context, "symmetrical" means that the masks used to mask the charges of the terminal phosphate have the same structure. However, it has been found that the percentage of the desired diphosphate or triphosphate species of the active substance that is released by chemical or enzymatic hydrolysis depends on the speed with which the first mask is cleaved to release the monomasked intermediate. The corresponding products of hydrolysis of the pyrophosphate group were detected as a by-product, in the case of the nucleosidediphosphate prodrugs these were the nucleoside monophosphates, in the case of the nucleosidetriphosphates the corresponding nucleosidediphosphate and nucleoside monophosphates. Ultimately, this merely results in a non-selective release of the desired target compound.

Jessen et al. 2008 and Schulz et al. 2014 (H. J. Jessen, T. Schulz, J. Balzarini, C. Meier, Bioreversible protection of nucleosidediphosphates; Angewandte Chemie [Applied Chemistry] International Edition English 2008, 47, 8719-8722; T. Schulz, J. Balzarini, C. Meier, The DiPPro Approach: Synthesis, Hydrolysis, and Antiviral Activity of Lipophilic d4T Diphosphate Prodrugs; ChemMedChem 2014, 9, 762-75; see also Schulz, T., 2012, Synthese und Untersuchung von Nucleosiddiphosphat Prodrugs [Synthesis and Analysis of Nucleosidediphosphate Prodrugs], Dissertation, Hamburg University) also describe symmetrically masked nucleosidediphosphates. Asymmetrical masking of a nucleosidediphosphate analogue (1-[(2R,5S)-5-(Hydroxymethyl)-2,5-dihydrofuran-2-yl]-5-methylpyrimidine-2,4-dion, stavudine, d4T) with an acyloxybenzyl group and a β-cyanoethyl group is also described in Schulz et al. 2014. However, the β-cyanoethyl mask can only be cleaved chemically, not enzymatically, which would be essential to enable its use as a pharmaceutical.

The object of the present invention is therefore to provide further improved di- and/or triphosphate prodrugs, in particular nucleotide and nucleotide analogue prodrugs, which do not have the drawbacks known from the prior art.

Surprisingly, it has proven possible to solve this problem with a suitable bioreversible asymmetrical masking of di- and triphosphate compounds, particularly of nucleoside diphosphates and nucleoside triphosphates and/or analogues thereof, wherein the masking is only carried out on the terminal, i.e., the β- or γ-phosphate, whereas masking of the internal phosphate is omitted. The invention yields significantly improved bioreversible masking of nucleosidediphosphates (NDP) and nucleosidetriphosphates (NTP) and of their analogues.

In order to solve this object, of the present invention provides in a first aspect a compound having general formula I

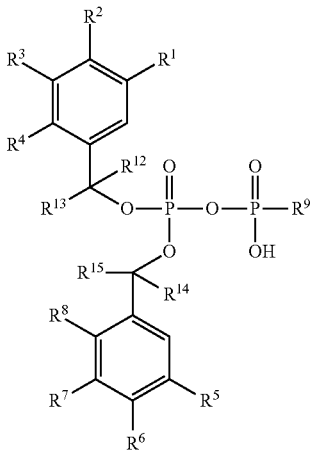

(I)

or a pharmaceutically acceptable salt thereof, wherein $R^1$, $R^3$, $R^5$ and $R^7$ are independently H, halogen, $NO_2$, CN, $SO_3H$, a substituted or unsubstituted cyclic, acyclic, linear or branched aliphatic or heteroaliphatic radical, or a substituted or unsubstituted aromatic or heteroaromatic radical, $R^2$ and $R^4$ are independently H or Z—C(Y)—$R_A$, but are not both H, $R^6$ and $R^8$ are independently H, Z—C(Y)—$R_B$, but are not both H, Z, Y is independently O, S or HN, $R_A$ and $R_B$ are different and each is a substituted or unsubstituted cyclic, acyclic, linear or branched aliphatic or heteroaliphatic radical, or a substituted or unsubstituted aromatic or heteroaromatic radical, $R^9$ is nucleoside, nucleoside monophosphate, nucleoside analogue, nucleoside monophosphate analogue, O—$R^{10}$, OP(O)(OH)—$R^{10}$ or OP(O)(OH)—O—$R^{10}$, wherein $R^{10}$ is a substituted or unsubstituted cyclic, acyclic, linear or branched aliphatic or heteroaliphatic radical, or a substituted or unsubstituted aromatic or heteroaromatic radical, $R^{12}$, $R^{13}$, $R^{14}$ and $R^{15}$ are independently H, a substituted or unsubstituted cyclic, acyclic, linear or branched aliphatic or heteroaliphatic radical, a substituted or unsubstituted aromatic or heteroaromatic radical, and/or an electron acceptor.

Among the compounds according to the invention, the benzyl derivative masks A and B

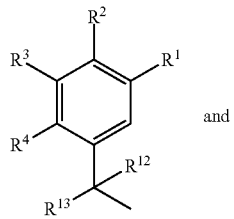

A and

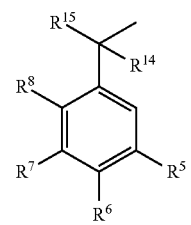

B on the terminal phosphate group differ in the radicals R on the phenyl ring in such manner that they can be cleaved in the cell selectively by enzymatic action in the cell, e.g., by esterases, to release the desired diphosphate or triphosphate compound. In order to achieve the desired selectivity, the masks are designed so that one of them is less stable than the other, that is to say it is cleaved faster, thereby enabling rapid formation of a monomasked intermediate with strong resistance to a nucleophilic attack on the phosphoric acid anhydride bond(s). The second group is more lipophilic, and thus provides the lipophilicity necessary to guarantee its uptake into the cell. Increased cleaving speed may be achieved for example by increasing the hydrophilicity (polarity) of the mask. A person skilled in the art is familiar with the technique of adjusting the hydrophilicity or lipophilicity of a mask, which can be determined if necessary by routine testing. For example, the lipophilicity of a mask may be influenced by the size or length of a hydrocarbon radical, its hydrophilicity by providing polar radicals. The stability of the mask may also be influenced by the inclusion of heteroatoms, for example.

The inventors found that the cleavage speeds of the two masks are often closely related to their lipophilicity, and particularly in such manner that the hydrolysis half-life period of the mask increases with increasing lipophilicity. Without wishing to be bound by a theory, it is assumed that lipophilicity is increased mainly by linking longer hydrophobic side chains, alkyl chains for example, which are then generally correspondingly less susceptible to attack by a nucleophil or enzyme due to steric inhibition. It should be noted, however, that the described correlation between the lipophilicity and stability (hydrolysis half-life period) of a mask is merely one indicator for the selection of suitable mask combinations. In some cases, even a more highly lipophilic mask can form the less stable mask in a certain combination. The person skilled in the art can determine this through routine experimentation.

The compounds according to the invention enable the inclusion of nucleotides and nucleotide analogues as well as other organic compounds with a hydroxyl group, e.g., of sugars or alcohols, at the level of di- and triphosphates in the cell. Nucleosidetriphosphates may thus be introduced directly into the cell, with the result that further intracellular phosphorylisation steps, which would otherwise be essential, are no longer needed. In this way, not only can the cell make more effective use of the implanted nucleosides, but side-effects such as those provoked by monophosphates can also be avoided. The compounds according to the invention may be used to advantage for example as medicinal products with antiviral as well as antitumoural effects. They are particularly suitable for use as medicinal products for the treatment of viral infections, particularly retroviruses such as HI viruses, influenza, haemorrhagic fever and hepatitis viruses. At the same time, the compounds are also suitable for analytical purposes in biochemical tests, since the phosphorylised metabolites are released inside the cell. This makes it possible to conduct analyses that could not be carried out before. For example, even non-nucleosidic alcohols can be transported into the cell and released there in the di- (e.g., isoprenyl diphosphate) or triphosphate form thereof.

The compounds according to the invention regularly exist as salts under physiological conditions. For this reason, in the following text one diphosphate compound Ia (left) and one triphosphate compound Ib (right) will be represented for exemplary purposes, wherein Cat$^+$ stands for a cation, for example ammonium, triethylammonium or tetrabutylammonium, and $R^1$ to $R^8$ and $R^{12}$ to $R^{15}$ are defined as above. Nucl stands for nucleoside or nucleoside analogue.

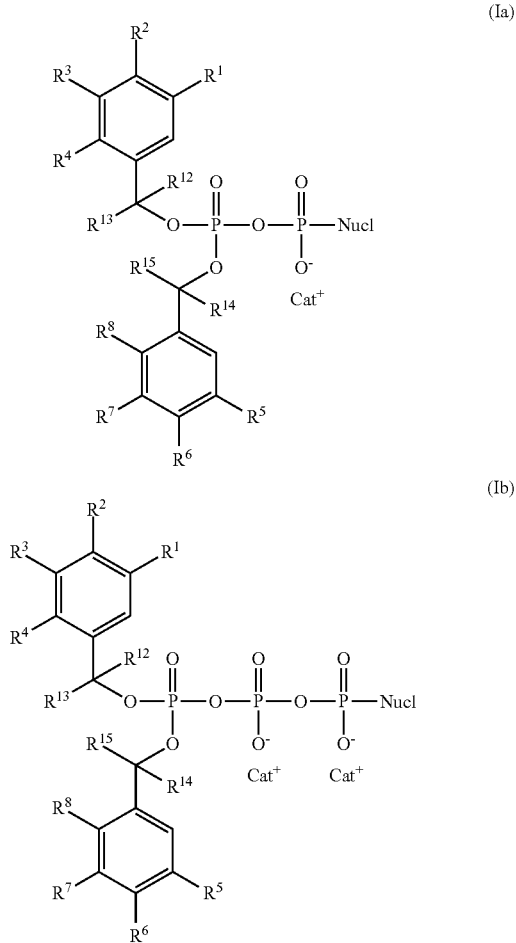

The term "asymmetrically masked di- or triphosphate compound" is understood to mean a compound according to the following formula,

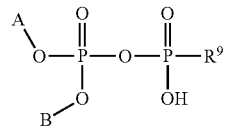

wherein A and B stand for different chemical structures, and $R^9$ is as defined above. The terminal phosphate group thus forms a stereogenic centre. The chemical structures A, B neutralise (mask) the negative electrical charges on the singly bound oxygen atoms of the terminal phosphate under physiological conditions. The masks themselves also do not carry a charge under physiological conditions. A terminal phosphate in the case of a diphosphate compound is understood to be the β-phosphate group, in a triphosphate compound the γ-phosphate group. In particular, in this context an "asymmetrically masked di- or triphosphate compound" is understood to be a compound in which one mask, e.g., mask A, is less stable and thus susceptible to faster enzymatic cleavage, while the other mask, e.g., mask B, is more lipophilic.

For the present purposes, an "enzymatically cleavable mask" is understood to be a mask that can be cleaved with the aid of enzymes that are present in the target cell or if necessary may be induced therein. The term also includes cases in which a mask is decomposed in multiple steps, for example in cascaded manner, and at least one decomposition step takes place by enzymatic action. For example, the initial attack may be enzymatic in nature, and the subsequent decomposition steps take place spontaneously. On the other hand, a "chemically cleavable mask" is a mask which is not cleaved or substantially not cleaved or only very slowly cleaved under the condition prevailing in a target cell, in terms of temperature, pH value or salt content, for example.

For the present purposes, "nucleosides" are understood to be molecules consisting of a sugar radical (sugar component) and an organic base (base component), e.g., a heterocyclic organic base, particularly a nitrogenous heterocyclic base (nucleobase), which are bound by a glycosidic bond. The sugar radical is often a pentose, e.g., desoxyribose or ribose, but may also be another sugar, e.g., a $C_3$-, $C_4$- or $C_6$-sugar. Nucleobases are often, but not exclusively, purines (R) or pyrimidines (Y). Examples of naturally occurring purines are guanine (G) and adenine (A), examples of naturally occurring pyrimidines are cytosine (C), thymine (T) and uracil (U). Accordingly, a nucleoside is particularly understood to be a compound having general formula

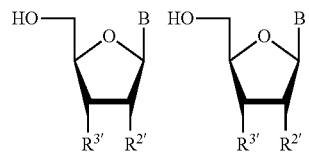

wherein B is a nitrogenous heterocyclic organic base, e.g., a nucleobase, and $R^{2'}$ and $R^{3'}$ are independently H or OH. Phosphorylised nucleosides, for example nucleoside monophosphate (NMP), nucleosidediphosphate (NDP) and nucleosidetriphosphate (NTP), are also called nucleotides. The phosphate, diphosphate (pyrophosphate) and triphosphate groups are typically linked to the 5'-C atom of the sugar component in the nucleoside. However, the invention also embraces compounds in which the phosphate group(s) are bound to a 2'- or 3'-OH group.

For the present purposes, a "nucleoside analogue" is understood to be an organic compound that does not occur naturally in the human body, but is structurally similar to a nucleoside that does occur naturally in the human body, so it can be processed by the cell for example, and/or by viral enzymes in essentially the same way as a natural nucleoside, phosphorylised, for example, and incorporated in a RNA- or DNA-strand. A nucleoside analogue may itself be a nucleoside. However it may also be another compound with the same properties as above, for example, such as a compound of a heterocyclic base and an acyclic radical and/or a radical that is not a sugar, or a compound of a carbocyclic compound and a heterocyclic base. In the case of carbocyclic nucleoside analogues, for example, the ring oxygen is replaced in the sugar component by a carbon (a methylene group or a substituted methylene group). In the sugar component a C atom may also be replaced by a heteroatom for example, for example the 3'-C atom may be replaced with sulphur. Nucleoside analogues are either nucleosides themselves, as defined above, or structurally and/or functionally similar to nucleosides. Since nucleoside analogues do not necessarily have to contain a sugar or base component in a more narrow sense, this definition may also include a component similar to the base component (a base analogue) or a component similar to the sugar component (sugar analogue) if necessary. Where a sugar component or base component is mentioned in this document, it is intended to denote the corresponding analogue components of nucleoside analogues as well, unless the context expressly indicates otherwise.

Many nucleoside analogues are known to the person skilled in the art. Known examples are AZT (3'-azido-2',3'-didesoxythimidine, azidothymidine), 2',3'-didesoxyinosin (Didanosine), 2',3'-didesoxycytidine (Zalcitabine), P3-L-2', 3'-didesoxythiacytidine (Lamivudine, 3TC), L-thymidine, 2'-methyl-("up")-2'-hydroxyl-("down")-uridine/-cytidine, 2'-methyl-("up")-2'-fluoro-("down")-uridine/-cytidine (see for example U.S. Pat. No. 7,608,600 B1), 2-amino-9-((2-hydroxyethoxy)methyl)-1H-purin-6(9H)-one (Acyclovir).

For the present purposes, a "nucleosidephosphate analogue" is understood to be an analogue of phosphorylised nucleoside, i.e. a nucleotide analogue, a "nucleoside monophosphate analogue" is thus an analogue of a nucleoside monophosphate. Examples of nucleoside monophosphate analogues are nucleoside phosphonates such as 3-hydroxy-2-phosphonomethoxypropyl (HPMP), 2-phosphonomethoxyethyl (PME), 2',3'-didehydro-2',3'-dideoxythymidine-phosphonate (d4TP), (S)-9-(3-hydroxy-2-phosphonylmethoxypropyl)adenine (HPMPA) and 9-(2-phosphonylmethoxyethyl)adenine (PMEA, Adefovir). Nucleosidephosphonates are known to the person skilled in the art, contain a C—P bond instead of the P—O bond of nucleoside phosphates, and may contain for example a nucleobase, an acyclic or cyclic aliphatic sugar analogue component and a phosphonomethyl group $CH_2P(O)(OH)_2$ group (see for example Pertusati et al. 2012, Medicinal Chemistry of Phosphonate Prodrugs for Antiviral Therapy, Antivir Chem Chemother. 22:181-203, doi: 10.3851/IMP2012). Phosphorylised nucleoside analogues such as phosphorylised nucleosides with a modified nucleobase also fall within the meanings of the terms "nucleosidephosphate analogue" or "nucleotide analogue".

If the abbreviation "Nucl" is used in this document, it includes both nucleosides and nucleoside analogues. Unless expressly indicated otherwise, the abbreviations "NMP", "NDP" and "NTP" include not only nucleoside monophosphates, nucleosidediphosphates and nucleosidetriphosphates, but also the corresponding analogues, that is to say nucleoside monophosphate analogues, nucleosidediphosphate analogues and nucleosidetriphosphate analogues.

For the present purposes, range values such as "1-10" are always to be understood to include the disclosure of all intermediate values as well. In the event that a cited value that can only refer to integers, such as a number of C atoms, for example, this means that only integers are disclosed. Any smaller range within the main range may also be considered to be disclosed therewith, wherein the reference to the smaller range is also understood to include ranges that do not include any of the limit values of the range.

The expression "$C_n$-$C_m$," or "$C_{n-m}$", wherein n and m are each positive integers and m is greater than n, stands for a range indicating the number of C atoms of a compound or radical. Here, the expression is explicitly intended to include all intermediate integers between the range limits n and m, each being independent of the others. Thus for example, the expression "$C_{1-10}$" (n=1, m=10) means a compound, a group or a radical with 1-10, i.e. 1, 2, 3, 4, 5, 6, 7, 8, 9 or 10 C atoms. "$C_{1-10}$" therefore also simultaneously comprises for example "$C_{2-6}$", i.e. 2, 3, 4, 5 or 6 C atoms, or "$C_{1-4}$", i.e. 1, 2, 3 or 4 C atoms, or "$C_{4-9}$", i.e. 4, 5, 6, 7, 8 or 9 C atoms. Similarly, the term "$C_{1-20}$-alkyl" means for example an alkyl group with 1, 2, 3, 4, 5, 6, 7, 8, 9, 10, 11, 12, 13, 14, 15, 16, 17, 18, 19 or 20 C atoms and comprises all combinations of the values of n and m that lie within the range from n=1 to m=20, e.g., "$C_{1-10}$-Alkyl", i.e. an alkyl with 1, 2, 3, 4, 5, 6, 7, 8, 9 or 10 C atoms, or "$C_{5-7}$-alkyl", i.e. and alkyl with 5, 6 or 7 C atoms. The same also applies for terms such as "$C_{2-10}$-alkenyl", "$C_{4-20}$-alkeninyl" and the like.

The term "aliphatic radical" comprises cyclic or acyclic, linear (straight-chain) or branched, saturated or unsaturated carbon compound radicals with the exception of aromatic radicals. The term "heteroaliphatic radical" means aliphatic radicals with carbon skeletons in which one or more C atoms are replaced by heteroatoms, for example oxygen, sulphur, nitrogen or phosphorus.

The term "alkyl" includes saturated aliphatic (non-aromatic) groups, including straight-chain (linear) alkyl groups (e.g., methyl, ethyl, propyl, butyl, pentyl, hexyl, heptyl and octyl) and branched alkyl groups (e.g., isopropyl, tert-butyl, isobutyl). The term also includes O-, N-, S- or P-alkyl groups (e.g., —O-methyl), i.e. alkyl groups that are bound to a compound by an atom of oxygen, nitrogen-, sulphur or phosphorus.

The term "alkenyl" includes unsaturated aliphatic (non-aromatic) groups with at least one C—C double bond, including straight-chain and branched alkenyl groups. The term also includes O-, N-, S- or P-alkenyl groups (e.g., —O-propenyl), i.e. alkenyl groups that are bound to a compound by an atom of oxygen, nitrogen-, sulphur or phosphorus.

The term "alkinyl" includes unsaturated aliphatic (non-aromatic) groups with at least one C—C triple bond, including straight-chain and branched alkenyl groups. The term also includes O-, N-, S- or P-alkinyl groups (e.g., —O-butinyl), i.e. alkinyl groups that are bound to a compound by an atom of oxygen, nitrogen-, sulphur or phosphorus.

The term "alkeninyl" includes unsaturated aliphatic (non-aromatic) groups with at least one C—C double bond and at least one C—C triple bond, including straight-chain and branched alkeninyl groups. The term also includes O-, N-, S- or P-alkeninyl groups i.e. alkeninyl groups that are bound to a compound by an atom of oxygen, nitrogen-, sulphur or phosphorus, The term "cycloalkyl" includes alicyclic, i.e. ring-shaped saturated aliphatic (non-aromatic) groups, e.g., cyclopropyl, cyclopentyl, cyclohexyl, cycloheptyl, cyclooctyl. The term further comprises O-, N-, S- or P-cycloalkyl groups, i.e. cycloalkyl groups that are bound to a compound by an atom of oxygen, nitrogen, sulphur or phosphorus. Similarly, the terms "cycloalkenyl", "cycloalkinyl" and "cycloalkeninyl" mean ring-shaped aliphatic (non-aromatic) alkenyls, alkinyls or alkeninyls as defined above, wherein the double and/or triple bond(s) may be present inside or outside the ring or ring system.

The term "heteroalkyl" denotes alkyl groups in which one or more carbon atoms of the carbon skeleton have been replaced with other atoms (heteroatoms), e.g., atoms of oxygen, nitrogen, sulphur or phosphorus. The term further comprises O-, N-, S- or P-heteroalkyl groups, i.e. heteroalkyl groups that are bound to a compound by an atom of oxygen, nitrogen, sulphur or phosphorus. The term "heteroalkyl" also comprises cycloalkyls in which one or more carbon atoms of the hydrocarbon skeleton have been replaced with other atoms (heteroatoms), e.g., atoms of oxygen, nitrogen, sulphur or phosphorus. Under the terms "heteroalkenyl", "heteroalkinyl" "heteroalkeninyl" are correspondingly to be understood alkenyls, alkinyls and alkeninyls as well as cycloalkenyls, cycloalkinyls and cycloalkeninyls, in which one or more carbon atoms of the hydrocarbon skeleton are replaced with other atoms (heteroatoms), e.g. oxygen, nitrogen, sulfur or phosphorus atoms. For example, the term "$C_{1-20}$-heteroalkyl" means an alkyl group with 1, 2, 3, 4, 5, 6, 7, 8, 9, 10, 11, 12, 13, 14, 15, 16, 17, 18, 19 or 20 C atoms and at least one heteroatom. The same also applies correspondingly for heteroalkenyls, heteroalkinyls and heteroalkeninyls.

The term "aryl" is understood to include groups with aromaticity, including multi-member aromatic single ring groups and multicyclic systems with at least one aromatic ring. Examples of aryl groups include benzene, phenyl and naphthalene. The term further comprises O—, N—, S—or P-aryl groups, i.e. aryl groups that are bound to a compound by an atom of oxygen, nitrogen, sulphur or phosphorus. For the present purposes, the term "aromatic radical" is used synonymously with "aryl".

The term "heteroaryl" is understood to include aryl groups which have heteroatoms in the ring structure, i.e. in which one or more carbon atoms in the ring structure have been replaced by other atoms (heteroatoms), e.g., oxygen, nitrogen, sulphur or phosphorus atoms. Examples of heteroaryls are pyrrole, furan, thiophene, thiazole, isothiazole, imidazole, triazole, tetrazole, pyrazole, oxazole, pyridine, pyrazine, pyridazine and pyrimidine. The term further comprises multicyclic aryl groups, e.g., bicyclic and tricyclic, e.g., benzoxazole, benzodioxazole, benzothiazole, benzoimidazole, benzothiophene, methylenedioxyphenyl, quinoline, isoquinoline, indole, benzofuran, purine or benzofuran. The term further comprises O—, N—, S—or P-heteroaryl groups, i.e. heteroaryl groups that are bound to a compound by an atom of oxygen, nitrogen, sulphur or phosphorus. The term "heteroaromatic radical" is used synonymously with "heteroaryl" here.

For the present purposes, the term "halogen" is understood to include chlorine (Cl), fluorine (F), bromine (Br) and iodine (I), particularly chlorine (Cl) and fluorine (F).

The term "substituted" means that one or more substituents are present which replace a hydrogen atom on one or more carbon atoms of the hydrocarbon skeleton or on one or more heteroatoms in the carbon skeleton. Examples of such substituents are oxo-, hydroxyl-, phosphate-, cyano-, azido- and amino groups, but they may also be for example halogens (e.g., F, Cl), alkyl-, cycloalkyl-, heteroalkyl-, heterocycloalkyl-, aryl- and heteroaryl groups.

For the present purposes, an "electron acceptor" is understood to be a compound, a compound radical or a functional group that attracts electrons to itself and thus brings about a charge shift, i.e. polarisation in a compound. Electron acceptors and electron acceptor groups are known to the person skilled in the art and have for example a negative inductive or mesomeric effect. Examples of electron acceptor groups are OMe, MeSO$_2$, =O, C(O)H, COOH, CN, SO$_3$H, ketones, esters and the ester group, NO$_2$ and halogen (e.g., F, Cl). Me stands for methyl.

Radical $R^9$ is bound via an oxygen atom in all cases, in the case of a nucleoside monophosphate or nucleoside monophosphate analogue preferably an oxygen of the phosphate or phosphonate group. In order to avoid misunderstandings, it is to be clarified that OP(O)(OH)—$R^1$ and OP(O)(OH) O—$R^{10}$ stand for radicals according to the following formulas

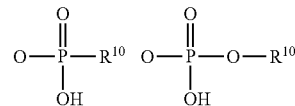

wherein $R^{10}$ is defined as above. In order to further avoid misunderstandings, it should be noted that the nucleoside or nucleoside analogue is bound to the respective phosphorus atom via an oxygen atom of the sugar component, on the C5 atom of a pentose for example. In case of a pentose, the bond is preferably created via the OH group on the 5'-C atom. However, the bond may also be made via an oxygen atom on the 2'- or 3'-C atom. O—$R^{10}$ may also be referred to as an "alcohol radical" here, in which case this is understood to include any organic carbon compound in which a hydrogen atom is replaced with a hydroxyl group on the carbon skeleton. Examples of alcohols include sugars such as glucose, fructose, mannose etc., but also other compounds such as geraniol.

In a preferred embodiment of the invention, the radicals $R^1$, $R^3$, $R^5$ and $R^7$ in the compound according to formula I above are each independently H, halogen, NO$_2$, CN, SO$_3$H, or a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, particularly preferably independently H or a substituted or unsubstituted cyclic, acyclic, linear or branched $C_{1-10}$-aliphatic radical $C_{1-10}$-heteroaliphatic radical, or a substituted or unsubstituted $C_{5-12}$-aromatic radical or $C_{3-12}$-heteroaromatic radical.

In a further preferred embodiment of the invention, $R^1$, $R^3$, $R^5$ and $R^7$ in the compound according to formula I above are each independently selected from the group consisting of H, halogen, NO$_2$, CN, SO$_3$H, substituted or unsubstituted $C_{1-20}$-alkyl, substituted or unsubstituted $C_{2-20}$-alkenyl, substituted or unsubstituted $C_{2-20}$-alkinyl, substituted or unsubstituted $C_{4-20}$-alkeninyl, substituted or unsubstituted $C_{3-20}$-cycloalkyl, substituted or unsubstituted $C_{3-20}$-cycloalkenyl, substituted or unsubstituted $C_{5-20}$-cycloalkinyl, substituted or unsubstituted $C_{5-20}$-cycloalkeninyl, substituted or unsubstituted $C_{1-20}$-heteroalkyl, substituted or unsubstituted $C_{2-20}$-heteroalkenyl, substituted or unsubstituted $C_{2-20}$-heteroalkinyl, substituted or unsubstituted $C_{4-20}$-heteroalkeninyl, substituted or unsubstituted $C_{5-24}$-aryl, substituted or unsubstituted $C_{3-24}$-heteroaryl.

More preferably, $R^1$, $R^3$, $R^5$ and $R^7$ in the compound according to formula I above are each independently selected from the group consisting of H, halogen, $NO_2$, CN, $SO_3H$, substituted or unsubstituted $C_{1-10}$-alkyl, substituted or unsubstituted $C_{2-10}$-alkenyl, substituted or unsubstituted $C_{2-10}$-alkinyl, substituted or unsubstituted $C_{4-10}$-alkeninyl, substituted or unsubstituted $C_{3-10}$-cycloalkyl, substituted or unsubstituted $C_{3-10}$-cycloalkenyl, substituted or unsubstituted $C_{5-10}$-cycloalkinyl, substituted or unsubstituted $C_{5-10}$-cycloalkeninyl, substituted or unsubstituted $C_{1-10}$-heteroalkyl, substituted or unsubstituted $C_{2-10}$-heteroalkenyl, substituted or unsubstituted $C_{2-10}$-heteroalkinyl, substituted or unsubstituted $C_{4-10}$-heteroalkeninyl, substituted or unsubstituted $C_{5-12}$-aryl, substituted or unsubstituted $C_{3-12}$-heteroaryl. Particularly preferably, $R^1$, $R^3$, $R^5$ and $R^7$ are all H.

$R^{10}$ is preferably a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, particularly preferably are independently H, or a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, more preferably $C_{1-20}$-alkyl or $C_{1-20}$-alkenyl or a sugar radical.

Radicals $R^{12}$, $R^{13}$, $R^{14}$ and $R^{15}$ are preferably
i. each independently H, a substituted or unsubstituted cyclic, acyclic, linear or branched $C_{1-20}$-aliphatic radical or $C_{1-20}$-heteroaliphatic radical, a substituted or unsubstituted $C_{5-20}$-aromatic radical or $C_{3-20}$-heteroaromatic radical, and/or an electron acceptor, or
ii. each independently H, a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, or
iii. each independently selected from the group consisting of H, substituted or unsubstituted $C_{1-20}$-alkyl, substituted or unsubstituted $C_{2-20}$-alkenyl, substituted or unsubstituted $C_{2-20}$-alkinyl, substituted or unsubstituted $C_{4-20}$-alkeninyl, substituted or unsubstituted $C_{3-20}$-cycloalkyl, substituted or unsubstituted $C_{3-20}$-cycloalkenyl, substituted or unsubstituted $C_{5-20}$-cycloalkinyl, substituted or unsubstituted $C_{5-20}$-cycloalkeninyl, substituted or unsubstituted $C_{1-20}$-heteroalkyl, substituted or unsubstituted $C_{2-20}$-heteroalkenyl, substituted or unsubstituted $C_{2-20}$-heteroalkinyl, substituted or unsubstituted $C_{4-20}$-heteroalkeninyl, substituted or unsubstituted $C_{5-24}$-aryl, substituted or unsubstituted $C_{3-24}$-heteroaryl, or
iv. each independently selected from the group consisting of H, substituted or unsubstituted $C_{1-10}$-alkyl, substituted or unsubstituted $C_{2-10}$-alkenyl, substituted or unsubstituted $C_{2-10}$-alkinyl, substituted or unsubstituted $C_{4-10}$-alkeninyl, substituted or unsubstituted $C_{3-10}$-cycloalkyl, substituted or unsubstituted $C_{3-10}$-cycloalkenyl, substituted or unsubstituted $C_{5-10}$-cycloalkinyl, substituted or unsubstituted $C_{5-10}$-cycloalkeninyl, substituted or unsubstituted $C_{1-10}$-heteroalkyl, substituted or unsubstituted $C_{2-10}$-heteroalkenyl, substituted or unsubstituted $C_{2-10}$-heteroalkinyl, substituted or unsubstituted $C_{4-10}$-heteroalkeninyl, substituted or unsubstituted $C_{5-12}$-aryl, substituted or unsubstituted $C_{3-12}$-heteroaryl, or
v. all H, or
vi. an electron acceptor or H, providing that $R^{12}$ and $R^{14}$ are each H, and $R^{13}$ and $R^{15}$ are each an electron acceptor, or $R^{13}$ and $R^{15}$ are each H, and $R^{12}$ and $R^{14}$ are each an electron acceptor.

The two masks "A" and "B" in the present invention preferably differ only in the radicals $R^2$ and/or $R^4$ and $R^6$ and/or $R^8$. The other radicals, i.e., radicals $R^1$, $R^3$, $R^5$ and $R^7$ and preferably also radicals $R^{12}$, $R^{13}$, $R^{14}$ and $R^{15}$ are preferably all the same, particularly preferably all H. More particularly preferably, the two masks only differ in their radicals $R^2$ and $R^6$ or only in their radicals $R^4$ and $R^8$, preferably only in their radicals $R^2$ and $R^6$.

$R^2$ and $R^4$ are independently H or Z—C(Y)—$R_A$, wherein the bond with the phenyl ring is created via Z, and wherein Z and Y stand for O, S or HN, providing that both radicals $R^2$ and $R^4$ are H. The same applies for radicals $R^6$ and $R^8$. In the case that Y=O, the following structures for example are conceivable for radicals $R^2$, $R^4$, $R^6$ and $R^8$:

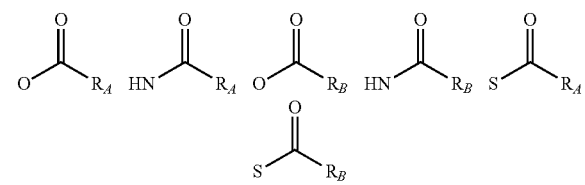

Preferably, only one of the radicals $R^2$ and $R^4$, preferably $R^2$, is Z—C(Y)—$R_A$, and the respective other radical, preferably $R^4$, is H, wherein Z—C(Y)—$R_A$ is preferably Z—C(O)—$R_A$. Similarly, preferably only one of the radicals $R^6$ and $R^8$, preferably $R^6$, is Z—C(Y)—$R_B$, and the respective other radical, preferably $R^8$, is H, wherein Z—C(Y)—$R_B$ is preferably Z—C(O)—$R_B$.

In a particularly preferred embodiment of compound I according to the invention, radical $R^2$ is Z—C(O)—$R_A$, and $R^6$ is Z—C(O)—$R_B$, while radicals $R^1$, $R^3$, $R^4$, $R^5$, $R^7$, $R^8$, $R^{12}$, $R^{13}$, $R^{14}$ and $R^{15}$ are each H, as in the following compound according to formula Ic:

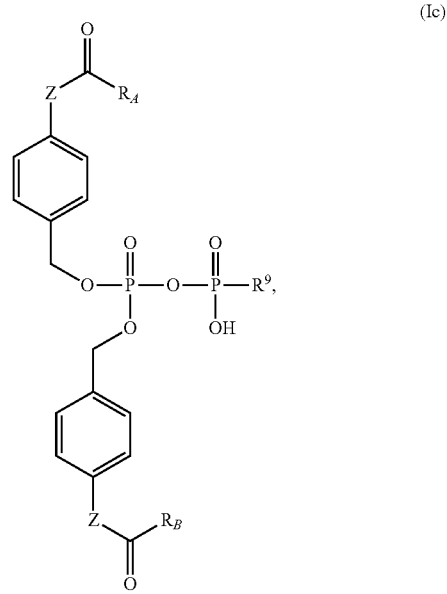

wherein Z=O, S or HN, preferably O, and $R^9$ is as defined above.

In the compound having general formula I according to the invention, radicals $R_A$ and $R_B$ are preferably independently a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, providing that radicals $R_A$ and $R_B$ are different.

Particularly preferably, radicals $R_A$ and $R_B$ are each independently selected from the group consisting of substituted or unsubstituted $C_{1-20}$-alkyl, substituted or unsubstituted $C_{2-20}$-alkenyl, substituted or unsubstituted $C_{2-20}$-alkinyl, substituted or unsubstituted $C_{4-20}$-Alkeninyl, substituted or unsubstituted $C_{3-20}$-Cycloalkyl, substituted or unsubstituted $C_{3-20}$-Cycloalkenyl, substituted or unsubstituted $C_{5-20}$-Cycloalkinyl, substituted or unsubstituted $C_{5-20}$-cycloalkeninyl, substituted or unsubstituted $C_{1-20}$-heteroalkyl, substituted or unsubstituted $C_{2-20}$-heteroalkenyl, substituted or unsubstituted $C_{2-20}$-heteroalkinyl, substituted or unsubstituted $C_{4-20}$-heteroalkeninyl, substituted or unsubstituted $C_{5-24}$-aryl, substituted or unsubstituted $C_{3-24}$-heteroaryl, preferably $C_{1-20}$-Alkyl or $C_{1-20}$-Alkenyl, provided that radicals $R_A$ and $R_B$ are different. Radicals $R_A$ and $R_B$ are particularly preferably selected from substituted or unsubstituted $C_{1-20}$-alkyl and substituted or unsubstituted $C_{2-20}$-alkenyl, provided that radicals $R_A$ and $R_B$ are different.

In this context, radical $R_B$ is preferably selected such that it is more lipophilic than $R_A$. Conversely, radical $R_A$ is preferably selected such that it is more unstable, i.e. more readily cleaved by the action of enzymes. $R_A$ may be a $C_{1-5}$-alkyl, for example, whereas $R_B$ is a $C_{7-20}$-alkyl. $R_A$ may be a methyl (Me), propyl (Pr) or butyl (Bu), for example, whereas $R_B$ is Ph-CF$_3$, Ph-Me, $C_7H_{15}$, $C_9H_{19}$, $C_{11}H_{23}$ or 5-OAc-Man (Ph=phenyl, Me=methyl, OAc=acetoxy group, Man=mannose).

The prodrugs according to the invention are highly resistant to chemical hydrolyse in aqueous buffer systems, and have a marked susceptibility to enzymatic hydrolysis, resulting in the release of the active substance in human cell extracts. Accordingly, they satisfy important requirements for use as medicinal products, particularly as an antiviral medicinal product, for example antiretroviral medicinal product. For example, the compounds according to the invention may be used advantageously in medicinal products for treating HIV infections, influenza, hepatitis C and B or haemorrhagic fever.

Accordingly, in a further aspect the invention also relates to a pharmaceutical composition that comprises a compound according to the invention and a pharmaceutically acceptable carrier. Pharmaceutically acceptable carriers are known to the person skilled in the art, and comprise one or more liquid, semisolid or solid fillers, diluents or other substances that are suitable for administration to mammals, including humans.

The expression "carrier" within the meaning of the present invention describes any organic or inorganic, natural or synthetic substance that can be combined with the active substance to facilitate the application. Examples of such carrier include but are not limited to organic or inorganic solvents, starch, lactose, mannitol, methylcellulose, talcum, gelatin, agar-agar, calcium phosphate, magnesium stearate, animal and vegetable fats, higher molecular fatty acids or higher molecule polymers.

The expression "pharmaceutically acceptable" described any material that is essentially non-toxic to mammals, particularly to humans and does not substantially impair the effectiveness of the biological activity of the active substance. Such materials may be pharmaceutically acceptable concentrations of salts, buffer materials, preservatives or the like. Non-limiting examples of pharmaceutically acceptable carriers include magnesium carbonate, magnesium stearate, talcum, sugar, lactose, ethanol, glycerin, water, buffer solutions etc. In addition, the pharmaceutical composition may also contain auxiliary agents and/or diluents.

In a further aspect, the invention also relates to a pharmaceutical administration form that comprises a compound according to the invention and a pharmaceutically acceptable carrier. In this context, the administration form is particularly preferably designed for oral administration, for example as a tablet or capsule.

In still another aspect, the present invention relates to a method for producing a compound having general formula (I)

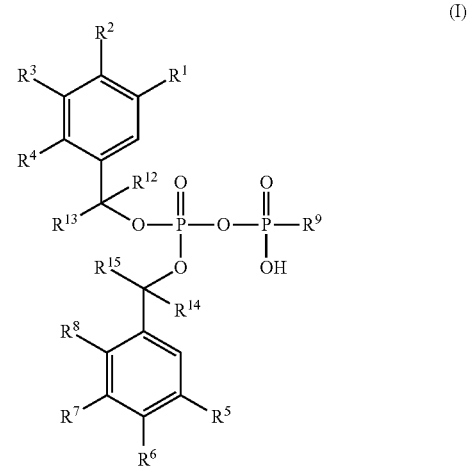

or a pharmaceutically acceptable salt thereof, wherein $R^1$, $R^3$, $R^5$ and $R^7$ are independently H, halogen, NO$_2$, CN, SO$_3$H, a substituted or unsubstituted cyclic, acyclic, linear or branched aliphatic or heteroaliphatic radical, or a substituted or unsubstituted aromatic or heteroaromatic radical, $R^2$ and $R^4$ are independently H or Z—C(Y)—$R_A$, but are not both H, $R^6$ and $R^8$ are independently H, Z—C(Y)—$R_B$, but are not both H, Z, Y is independently O, S or HN, $R_A$ and $R_B$ are different and each is a substituted or unsubstituted cyclic, acyclic, linear or branched aliphatic or heteroaliphatic radical, or a substituted or unsubstituted aromatic or heteroaromatic radical, $R^9$ is a nucleoside, nucleoside monophosphate, nucleoside analogue, nucleoside monophosphate analogue, O—$R^{10}$, OP(O)(OH)—$R^{10}$ or OP(O)(OH)—O—$R^{10}$, wherein $R^{10}$ is a substituted or unsubstituted cyclic, acyclic, linear or branched aliphatic or heteroaliphatic radical, or a substituted or unsubstituted aromatic or heteroaromatic radical, and wherein $R^{12}$, $R^{13}$, $R^{14}$ and $R^{15}$ are independently H, a substituted or unsubstituted cyclic, acyclic, linear or branched aliphatic or heteroaliphatic radical, a substituted or unsubstituted aromatic or heteroaromatic radical, and/or an electron acceptor, comprising the following steps:

a$_1$) reacting a compound having general formula II$_A$

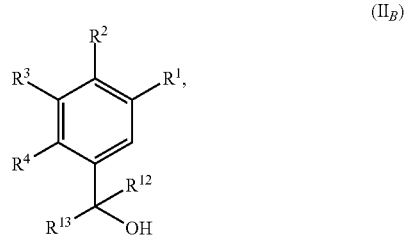

wherein R$^1$, R$^2$, R$^3$, R$^4$, R$^{12}$ and R$^{13}$ are defined as above, with i) phosphorus trichloride PCl$_3$ and N,N-diisopropylamine, or ii) bis(N,N-diisopropylamino)chlorophosphine to synthesise a compound having general formula III

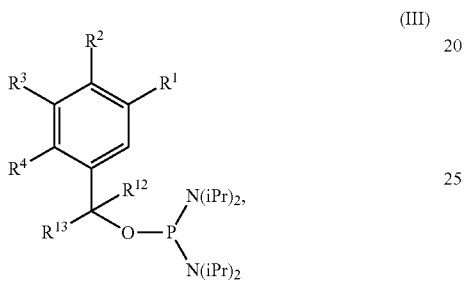

b$_1$) reacting the compound having formula III obtained in a) with a compound having general formula II$_B$

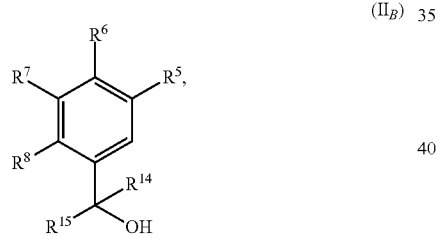

wherein R$^5$, R$^6$, R$^7$, R$^8$, R$^{14}$ and R$^{15}$ are defined as above, to synthesise a compound having general formula IV

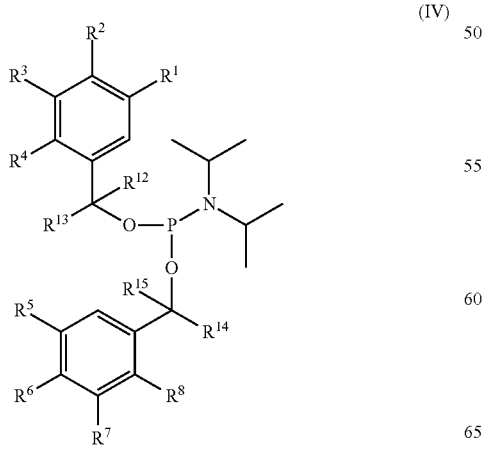

c$_1$) reacting the compound having formula IV obtained in b) with a compound according to general formula V

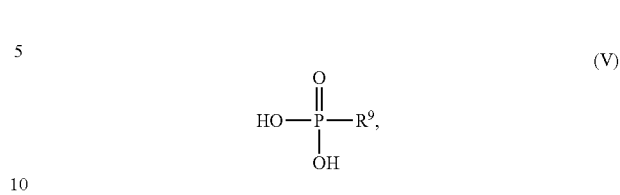

wherein R$^9$ is defined as above.

In an alternative variant, the method according to the invention comprises the following steps:

a$_2$) reacting a compound having general formula II$_A$

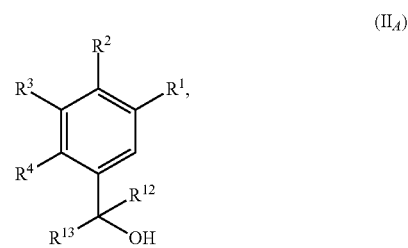

wherein R$^1$, R$^2$, R$^3$, R$^4$, R$^{12}$, and R$^{13}$ are defined as above, with diphenylphosphonate to synthesise a compound having general VI

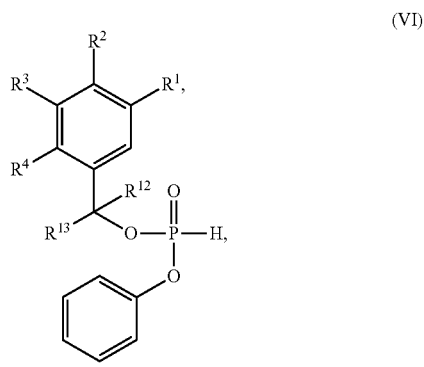

b$_2$) reacting the compound with formula VI obtained in a) with a compound having general formula II$_B$

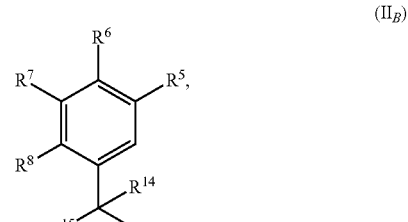

wherein R$^5$, R$^6$, R$^7$, R$^8$, R$^{14}$ and R$^{15}$ are defined as above, to synthesise a compound having general formula VII

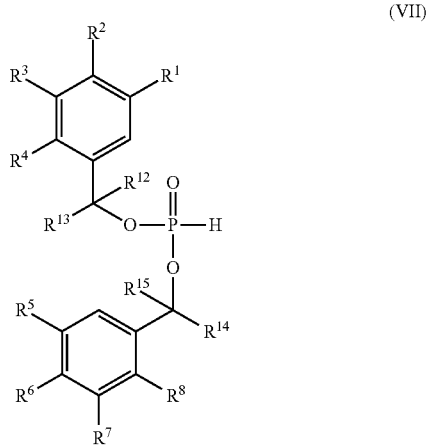

c$_2$) reacting the compound with formula VII obtained in b) with a compound according to general formula V

or ii) with phosphoric acid or a phosphoric acid salt and R$^9$ or a compound comprising R$^9$,
wherein R$^9$ is defined as above.

An example of a suitable phosphoric acid salt is tetrabutylammonium phosphate.

The alternative variant of the method according to the invention is particularly advantageous, because it is then possible to dispense with the use of the diphosphates and/or analogues thereof, which are often difficult to prepare, when synthesising nucleosidediphosphates and nucleosideriphosphates or analogues thereof, and to use corresponding monophosphates thereof instead, which are easier to prepare, and in some cases are even available commercially. In this variant, the compound according to formula VII is either reacted directly with a monophosphate compound to form a diphosphate compound, or first phosphorylised to form the corresponding pyrophosphate compound, which can then be reacted with a monophosphate compound. In this way, diphosphate compounds and particularly triphosphate compounds may be obtained without having to use diphosphate compounds. In this variant as well, however, of course the use of diphosphate compounds to prepare corresponding triphosphate compounds is not excluded, even though this is not preferred.

Preferred variants of the radicals R$^1$ to R$^{15}$ have been described previously in the discussion of the first aspect of the present invention, and are equally valid for the method aspects of the invention, so these will not be repeated here.

In the following, the invention will be explained in greater detail with reference to FIG. 1 and examples intended solely for illustrative purposes. In the drawing:

FIG. 1 is a schematic representation of the intracellular cleavage of the masks in an embodiment of the compound according to the invention.

FIG. 1 is a schematic representation of the assumed course of the release of a nucleosidediphosphate prodrug (NDP prodrug) according to an embodiment of the present invention in the cell. The two otherwise negatively charged oxygen atoms (shown in bold) of the hydroxyl groups of the terminal phosphate (in this case the β-phosphorus atom) are substituted asymmetrically in the NDP prodrug, i.e. masked with two different masks A and B (here different acyloxybenzyl derivatives). For this purpose, the radicals R$_A$ and R$_B$ differ with regard to their stability and lipophilicity. Radical R$_A$ is less stable than radical R$_B$, radical R$_B$ is more lipophilic than radical R$_A$. In the cell, the relatively unstable mask A is removed quickly following a rapidly completed enzymatic attack on the ester group by esterases (E) present in the cell and its subsequent spontaneous decomposition, resulting in a monomasked intermediate product. A nucleophilic attack (Nu$^-$=nucleophil) on the phosphorus anhydride bond with cleaving thereof does not occur, so the undesirable formation of the monophosphate is prevented. Mask B is also cleaved by the same mechanisms as mask A, but in a slower process, so that the unmasked nucleosidediphosphate prodrug is finally released in the cell.

EXAMPLES

A general schema for an embodiment of a method according to the invention for producing compounds I according to the invention is reproduced in the following. A first benzyl alcohol derivative II$_A$ is brought into reaction with phosphorus trichloride (PCl$_3$) to produce compound 100, which is reacted with N,N-diisopropylamine (NH(iPr)$_2$) to yield the corresponding phosphordiamidite compound III. Compound III is then brought to reaction with a second benzyl alcohol derivative II$_B$ in order to synthesise the phosphorodiamidite compound IV. This can then be coupled with a mono- or diphosphate compound V, a nucleoside monophosphate or nucleoside monophosphate analogue for example, either of which may optionally be denoted with the abbreviation NMP, or nucleoside diphosphate or nucleoside diphosphate analogue, which may optionally be denoted here with the abbreviation NDP, to yield compound I. NDP or NTP compounds according to the invention (including compounds containing nucleoside analogues) may also be denoted here optionally with the abbreviations DiPPro nucleotides or TriPPPro nucleotides.

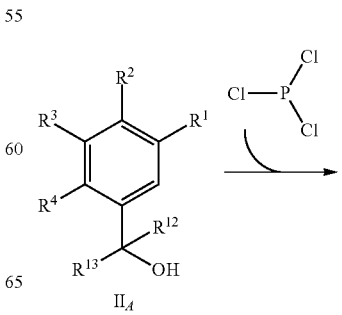

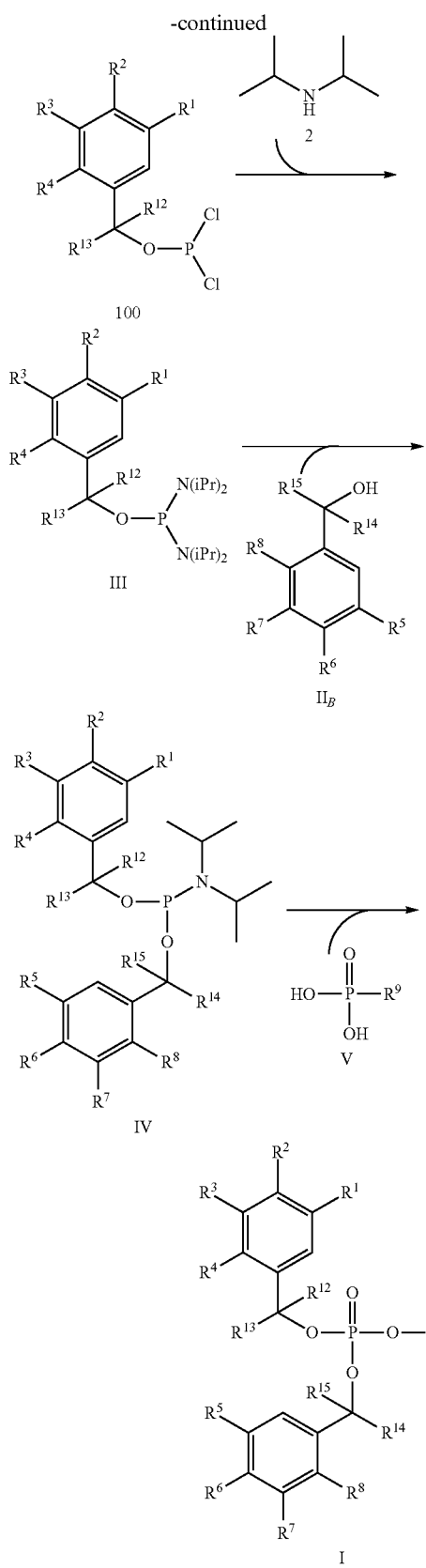

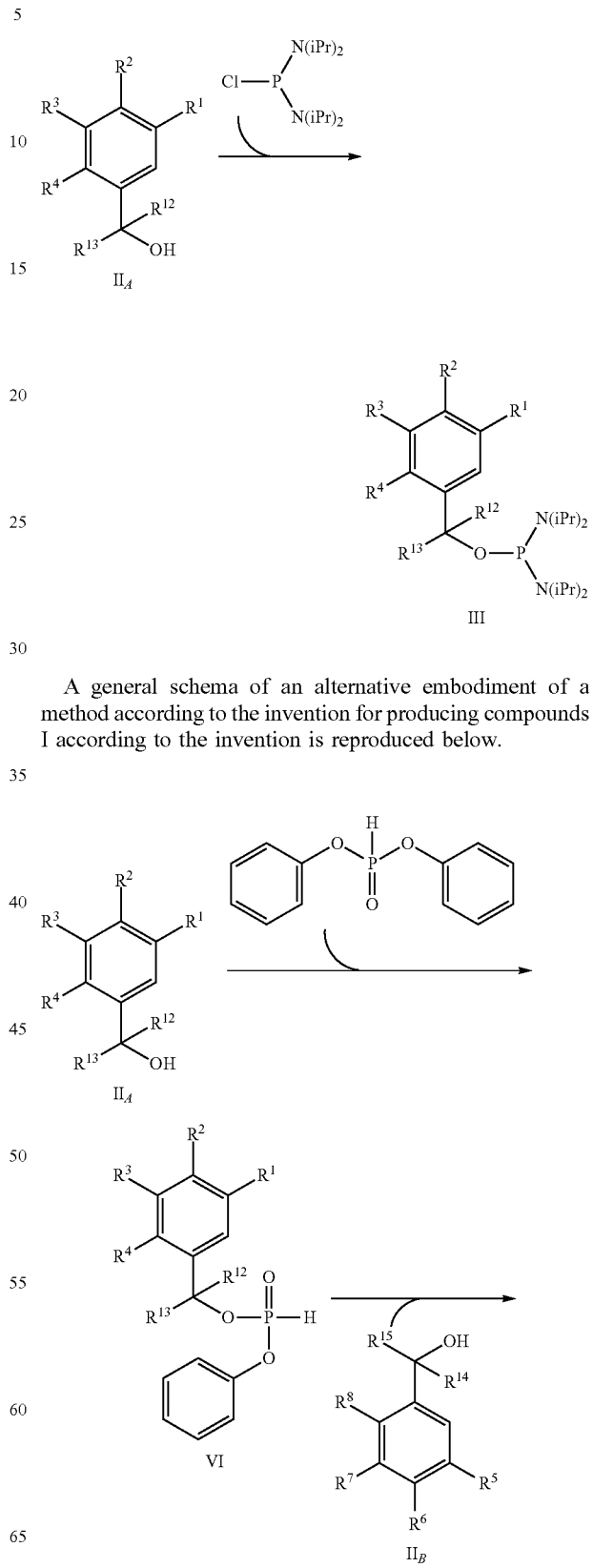

rophosphine according to the following general schema rather than with phosphorus trichloride ($PCl_3$) and N,N-diisopropylamine.

A general schema of an alternative embodiment of a method according to the invention for producing compounds I according to the invention is reproduced below.

In order to prepare phosphorodiamidite compound III, as an alternative the benzyl alcohol derivative $II_A$ can also be brought into reaction with bis(N,N-diisopropylamino)chlo-

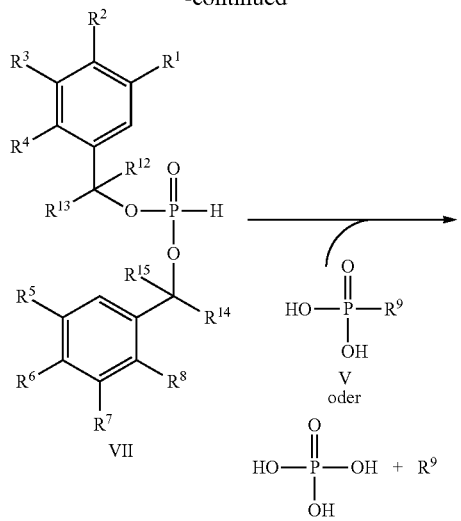

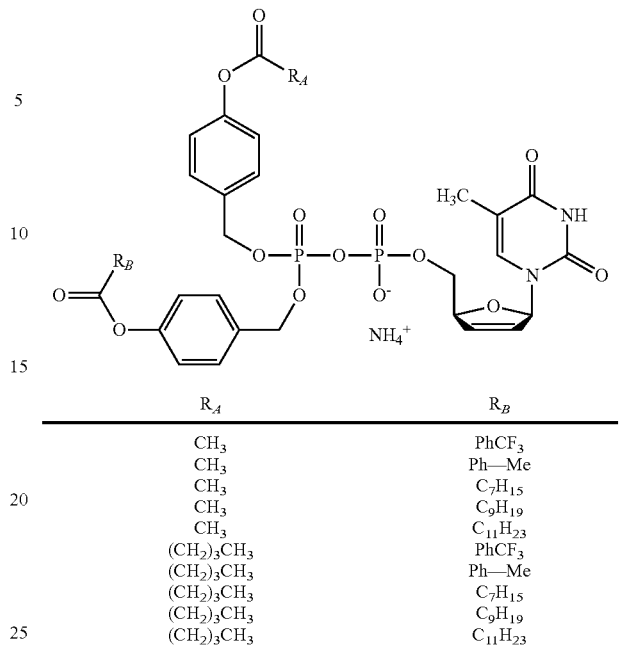

b) Zidovudine (AZT) as nucleoside analogue radical:

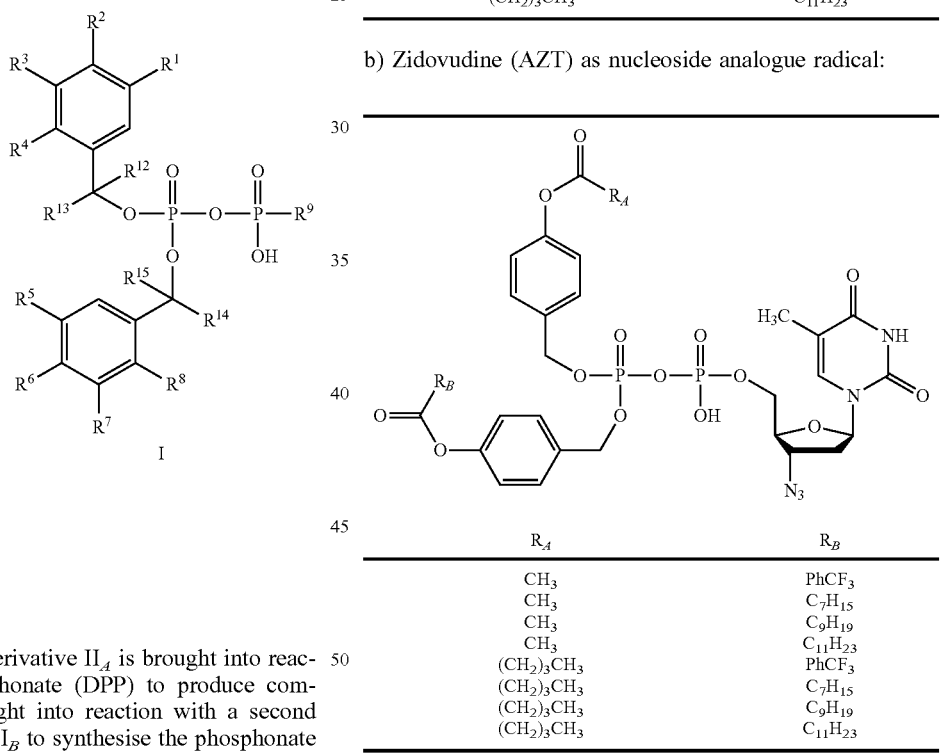

| $R_A$ | $R_B$ |
|---|---|
| $CH_3$ | $PhCF_3$ |
| $CH_3$ | $C_7H_{15}$ |
| $CH_3$ | $C_9H_{19}$ |
| $CH_3$ | $C_{11}H_{23}$ |
| $(CH_2)_3CH_3$ | $PhCF_3$ |
| $(CH_2)_3CH_3$ | $C_7H_{15}$ |
| $(CH_2)_3CH_3$ | $C_9H_{19}$ |
| $(CH_2)_3CH_3$ | $C_{11}H_{23}$ |

A first benzyl alcohol derivative $II_A$ is brought into reaction with diphenyl phosphonate (DPP) to produce compound VI, which is brought into reaction with a second benzyl alcohol derivative $II_B$ to synthesise the phosphonate compound VII. This may then be coupled with a mono- or diphosphate compound V, or first with phosphoric acid or a phosphoric acid salt and then with a $R^9$ compound or a compound containing $R^9$, a nucleoside monophosphate for example, so that compound I is obtained. A particular advantage of the last variant of this embodiment of the method according to the invention is triphosphate compounds can then be synthesised with the corresponding monophosphates, e.g., nucleoside monophosphates or analogues thereof.

Examples of DiPPro nucleotides produced in the method according to the invention are listed below:
a) Stavudine (d4T) as nucleoside analogue radical (Ph=phenyl; Me=methyl, OAc=acetoxy):

1. Production of Asymmetrically Masked Nucleoside Diphosphate and Nucleoside Triphosphate Compounds Using Phosphordiamidite Compounds In order to produce asymmetrically masked nucleoside diphosphate or nucleosidetriphosphate compounds (DiPPro-, TriPPPro-nucleotides) according to the invention, first the respective asymmetrical phosphoramidites are prepared according to the general method described above, so that then a coupling can be made with the desired nucleotide (analogue) (nucleoside monophosphate or nucleoside diphosphate(analogue)) to form asymmetrical NDP or NTP. By this method, a large number of asymmetrically masked nucleosidediphosphate or nucleoside-triphosphate compounds were represented successfully with very good yields. The coupling of the asymmetrical phosphoramidites with the respective nucleoside monophosphates and nucleoside diphosphates was optimised in an acid-activated reaction, so that many combinations of nucleoside diphosphate or nucleoside triphosphate compounds can be accessed in quantitative conversions and high isolated yields.

1.1 Synthesis of Phosphordiamidites
1.1.1 Synthesis Path 1

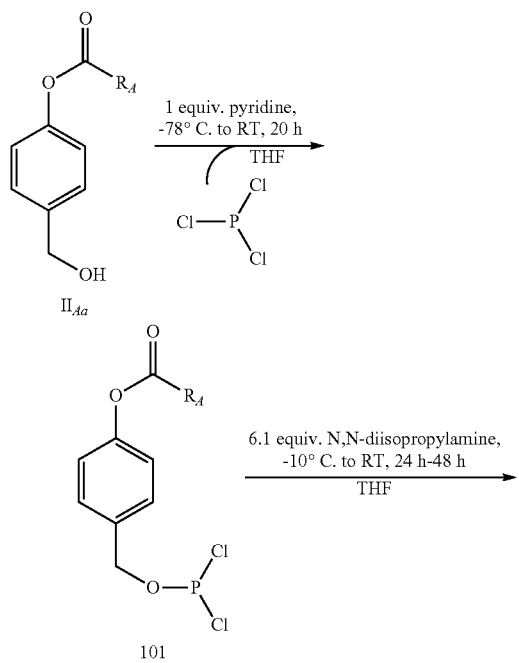

1 equivalent phosphorus trichloride and 1 equivalent pyridine are dissolved in a large quantity of tetrahydrofuran (THF, approx. 20 mL/g $PCl_3$) and cooled to $-78°$ C. in a nitrogen atmosphere. 1 equivalent of the phenyl ester $II_{Aa}$, also dissolved in THF, is added to this solution one drop at a time over a period of 1.5 h. After the addition by dripping, the cooler bath is removed, and the reaction mixture is stirred at room temperature (RT) for about 20 h until no more phenyl ester is detectable by TLC. Then 6.1 equivalents N,N-diisopropylamine are added one drop at a time at $-10°$ C. After removal of the cooler bath, the reaction mixture is stirred at room temperature. When the intermediate compound 101 has been completely converted, i.e. after about 24 to 48 h, the salts formed are removed by filtration and then the solvent at reduced pressure. Without any further processing, product IIIa is purified on the Chromatotron® with benzine/triethylamine as the eluent.

1.1.2 Synthesis Path 2

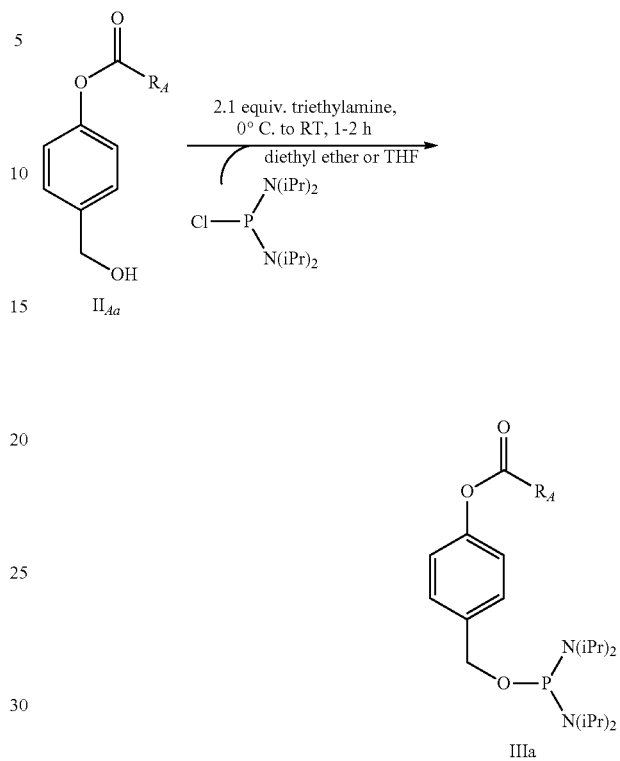

1 equivalent bis(N,N-diisopropylamino)-chlorophosphine is dissolved in diethylether or THF (12 mL/500 mg) in a nitrogen atmosphere. A solution of 2.1 equivalents triethylamine and 1.9 equivalents of the phenyl ester $II_{Aa}$, in diethylether or THF (corresponding to 5 mL) is added slowly with ice cooling. Then the cooler bath is removed and the reaction mixture is stirred at room temperature. After 1 to 2 hours, the triethylammonium chloride formed is removed by filtration and finally the solvent at reduced pressure. Without any further processing, product IIIa is purified on the Chromatotron® with benzine/triethylamine as the eluent.

1.2 Synthesis of Phosphoramidites

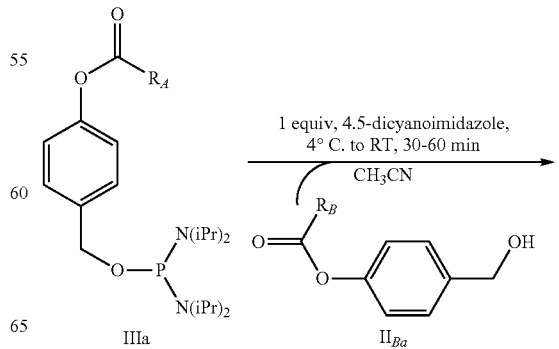

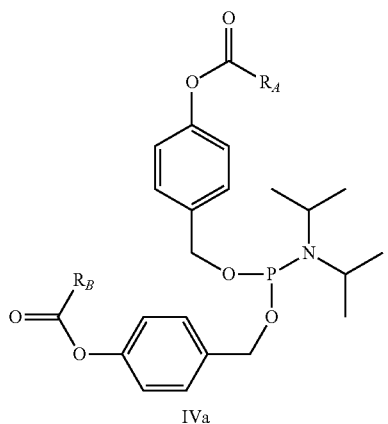

1.5 equivalents phosphordiamidite IIIa is first co-evaporated and finally dissolved in 2 mL/100 mg acetonitrile in a nitrogen atmosphere. A solution of 1 equivalent of the corresponding 4-acyloxybenzyl alcohol $II_{Ba}$ and 1 equivalent of a 0.25-molar 4,5-dicyanoimidazole activator solution in acetonitrile is added one drop at a time with ice cooling. After approx. 30 to 60 minutes stirring at room temperature, the reaction is ended by removing the solvent under reduced pressure. The residue is absorbed and filtered in benzine/triethylamine (9:1). The product IVa purified in the Chromatotron® with benzine/triethylamine as the eluent.

1.3 Synthesis of DiPPro-, TriPPPro-Nucleotides

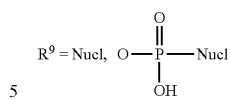

The reaction is carried out in a nitrogen atmosphere. 1 equivalent of the corresponding $N(C_4H_9)_4^+$ salt of the nucleoside monophosphate (NMP) or nucleosidediphosphate (NDP) is dissolved in acetonitrile (approx. 4 mL/100 g) and reacted with 1.5 equivalents of the phosphordiamidite IVa that was previously co-evaporated with acetonitrile. The phosphordiamidite IVa is activated by incremental addition of a 0.25 molar 4,5-dicyanoimidazole activator solution (in acetonitrile). 0.5 equivalents are added initially, and 0.25 equivalents are added every 5 min thereafter until complete conversion is achieved (not more than 1.75 equivalents). Oxidation is carried out by the addition of 1.5 equivalents of a 5.5 molar tBuOOH solution in n-decane. Reversed phase (RP) chromatography ("Puri Flash"), followed by ion exchange to form $NH_4^+$ and RP chromatography (Puri Flash) again, possibly several times, return the DiPPro-nucleotide or TriPPPro-nucleotide Ic in yields of up to 85%.

2. Production of Asymmetrically Masked Nucleoside Diphosphate and Nucleoside Triphosphate Compounds Using Phosphonate Compounds 2.1 Production of an Asymmetrically Substituted Phosphonate Compound

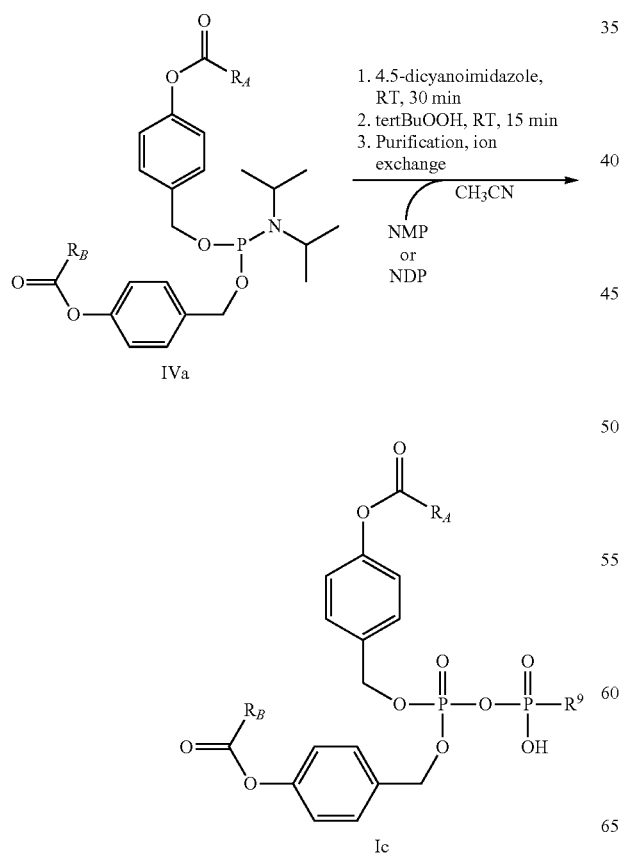

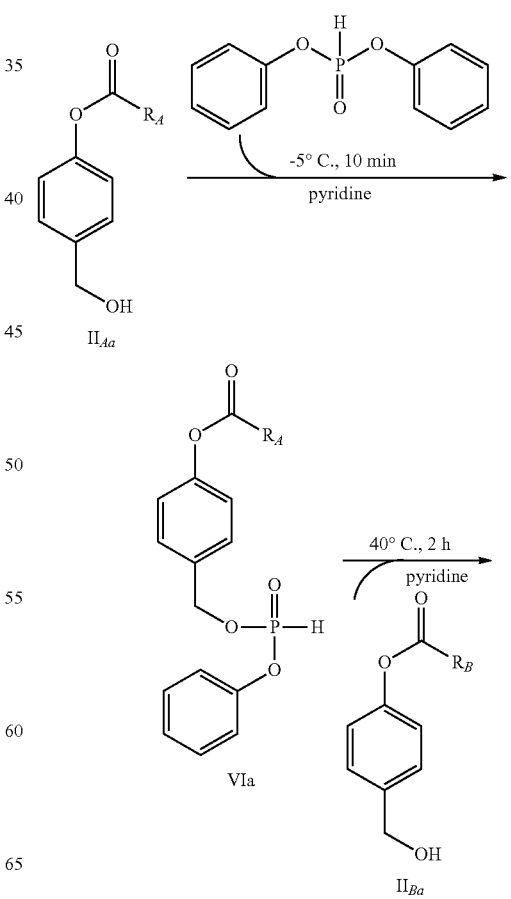

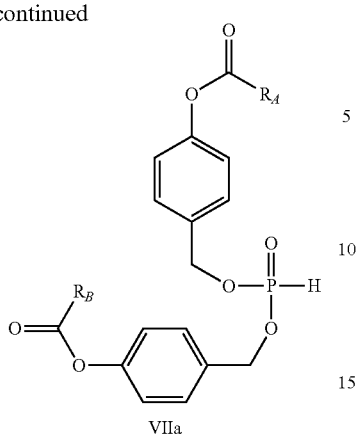

VIIa

To synthesise the asymmetrically substituted phosphonate compound VIIa, 1 equivalent phenyl ester $II_{Aa}$ in pyridine (approx. 15 mL/g $II_A$) is slowly added dropwise to a solution of 1,3 equivalents diphenyl phosphonate (DPP) in pyridine (approx. 20 mL/g DPP) that has been cooled to −5° C. in a nitrogen atmosphere. After stirring for ten minutes, 1,6 equivalents phenyl ester $II_{Ba}$ are added, and the solution is stirred for 2 h at 40° C. Then, all volatile components are removed at 40° C. in a high vacuum. The residue is also co-evaporated twice with toluene. Product VIIa is purified by chromatography with benzine/ethyl acetate/acetic acid as the eluent.

The resulting phosphonate compound VIIa may be brought into reaction with a nucleoside monophosphate or an analogue thereof to produce a nucleoside diphosphate or nucleoside diphosphate analogue (DiPPronucleotide(analogue)).

To produce nucleoside triphosphates (TriPPPro-nucleotides), first dibenzylpyrophosphate derivatives of compound VIIa are produced, and then the nucleoside triphosphate.

2.2 Production of Dibenzylpyrophosphate Derivatives of Compound VIIa

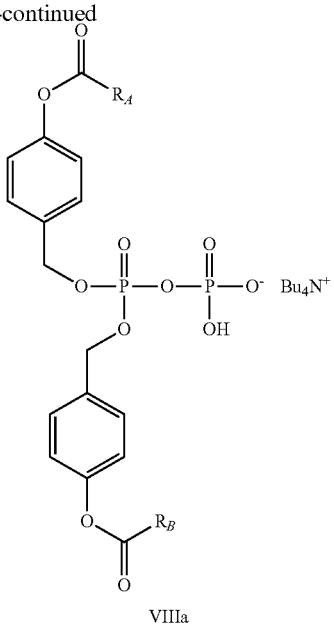

VIIIa 1 equivalent phosphonate VIIa is dissolved in acetonitrile (approx. 10 mL/g phosphonate), if necessary with slight warming and reacted with 2 equivalents N-chlorosuccinimide (NCS) in a nitrogen atmosphere. After an hour, the solution is immediately added dropwise to 2,5 equivalents tetra-n-butylammonium monophosphate in acetonitrile (approx. 20 mL/g phosphate salt). The solution is stirred for 1 h and then separated from the solvent. The residue is absorbed in dichloromethane and cold 1 M ammonium acetate solution, and the phases are separated with the aid of a centrifuge. The organic phase is washed with cold water again, dried over sodium sulphate, filtered and finally separated from the solvent. The desired product VIIIa is extremely pure. Conversion is quantitative.

2.3 Production of TriPPPro-Nucleotides

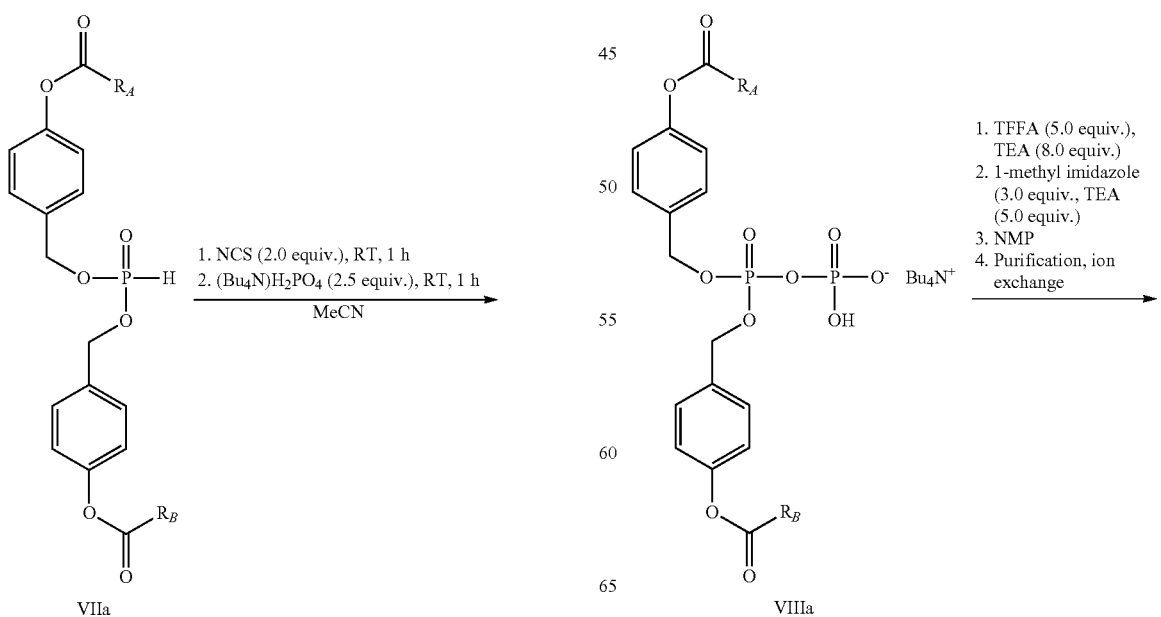

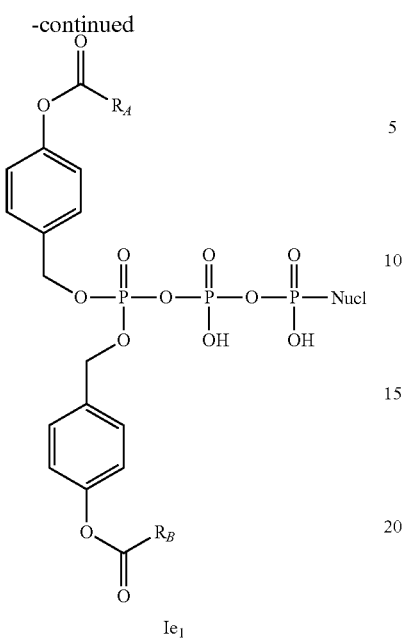

Ie₁

The reaction is conducted in a nitrogen atmosphere. First, 5 equivalents trifluoroacetic acid anhydride (TFAA) and 8 equivalents triethylamine (TEA) are mixed in acetonitrile (ca. 20 mL/g TFAA) at 0° C. This solution is then added to 1 equivalent dibenzylpyrophosphate compound VIIIa in acetonitrile (approx. 20 mL/g dibenzyl pyrophosphate). After 10 min at 0° C., all volatile components are removed in a high vacuum. The residue is suspended in acetonitrile (approx. 20 mL/g dibenzyl pyrophosphate) and reacted with 5 equivalents TEA and 3 equivalents methylimidazole. After stirring for five minutes, 1 equivalent of the corresponding $N(C_4H_9)_4^+$ salt of the nucleoside monophosphate (NMP, Nucl=nucleoside) dissolved in acetonitrile (approx. 20 mL/g NMP) is added, and the reaction is ended after 3 h by removal of the solvent at reduced pressure. Reversed phase (RP) chromatography ("Puri Flash"), followed by ion exchange to form $NH_4^+$ and RP chromatography (Puri Flash) again, possibly several times, return the TriPPPro-nucleotide Ie₁ in yields of up to 50%.

3. Hydrolysis Studies

Hydrolysis studies in CEM/0 cell extract have provided some insights into the enzymatic release of nucleoside diphosphates from prodrugs. The samples are incubated in cell extract and stopped at various times. The analysis of the hydrolysis samples was carried out by High Performance Liquid (HPL) chromatography. In two different groups on the acyl units of the masks, the less stable one is cleaved quickly (e.g., $R=CH_3$: $t_{1/2}$=approx. 2 min; $R=C_4H_9$: $t_{1/2}$=approx. 45 to 60 min), so that the more stable intermediate product forms. Then, the intermediate product hydrolyses quantitatively to the diphosphate. The formation of d4TDP was confirmed by co-injection of a d4TDP solution.

The chemical stability of the prodrugs was also tested in phosphate buffer at pH 7.3. For this purpose, solutions of the DiPPro and TriPPPro nucleotide are converted with a Sorensen type phosphate buffer (PBS), and the hydrolysis is monitored by HPL chromatography. The experiments show that all prodrugs are significantly more chemically stable than enzymatically stable (e.g., half-life periods of $CH_3$/$C_9H_{19}$-DiPPro-d4TDP (decomposition of the prodrug): $t_{1/2}$ (PBS)=48 h, $t_{1/2}$(CEM/0)=2 min). Because of the greater stability, the formation of the nucleoside monophosphate can also be observed at the beginning of the hydrolysis in phosphate buffer. But since the selection of an asymmetrical mask combines a less stable group with a highly lipophilic group, the intermediate product (and the more stable) forms very quickly as in the cell extract, so that diphosphate formation is strongly favoured.

The invention claimed is:

1. A compound having general formula I

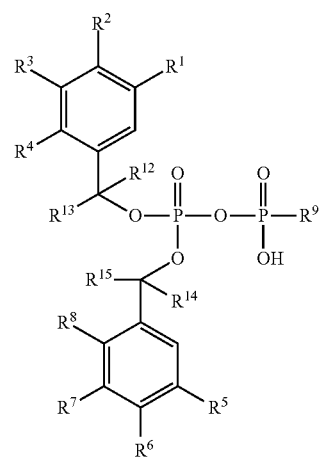

(I)

or a pharmaceutically acceptable salt thereof, wherein
$R^1$, $R^3$, $R^5$ and $R^7$ are independently H, halogen, $NO_2$, CN, $SO_3H$, a substituted or unsubstituted cyclic, acyclic, linear or branched aliphatic or heteroaliphatic radical, or a substituted or unsubstituted aromatic or heteroaromatic radical, $R^2$ and $R^4$ are independently H or $Z$—C(Y)—$R_A$, but are not both H, $R^6$ and $R^8$ are independently H, $Z$—C(Y)—$R_B$, but are not both H, Z, Y is independently O, S or HN, $R_A$ and $R_B$ are different and each is a substituted or unsubstituted cyclic, acyclic, linear or branched aliphatic or heteroaliphatic radical, or a substituted or unsubstituted aromatic or heteroaromatic radical, $R^9$ is nucleoside, nucleoside monophosphate, nucleoside analogue, nucleoside monophosphate analogue, O—$R^{10}$, OP(O)(OH)—$R^{10}$ or OP(O)(OH)—O—$R^{10}$, wherein $R^{10}$ is a substituted or unsubstituted cyclic, acyclic, linear or branched aliphatic or heteroaliphatic radical, or a substituted or unsubstituted aromatic or heteroaromatic radical, $R^{12}$, $R^{13}$, $R^{14}$ and $R^{15}$ are independently H, a substituted or unsubstituted cyclic, acyclic, linear or branched aliphatic or heteroaliphatic radical, a substituted or unsubstituted aromatic or heteroaromatic radical, and/or an electron acceptor.

2. The compound according to claim 1, wherein
a) $R^1$, $R^3$, $R^5$ and $R^7$
i. are each independently H, halogen, $NO_2$, CN, $SO_3H$, a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, or
ii. are each independently H, halogen, $NO_2$, CN, $SO_3H$, a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, or iii. are each independently selected from the group consisting of H, halogen, NO$_2$, CN, SO$_3$H, substituted or unsubstituted C$_{1-20}$-alkyl, substituted or unsubstituted C$_{2-20}$-alkenyl, substituted or unsubstituted C$_{2-20}$-alkynyl, substituted or unsubstituted C$_{4-20}$-alkeninyl, substituted or unsubstituted C$_{3-20}$-cycloalkyl, substituted or unsubstituted C$_{3-20}$-cycloalkenyl, substituted or unsubstituted C$_{5-20}$-cycloalkynyl, substituted or unsubstituted C$_{5-20}$-cycloalkeninyl, substituted or unsubstituted C$_{1-20}$-heteroalkyl, substituted or unsubstituted C$_{2-20}$-heteroalkenyl, substituted or unsubstituted C$_{2-20}$-heteroalkynyl, substituted or unsubstituted C$_{4-20}$-heteroalkeninyl, substituted or unsubstituted C$_{5-24}$-aryl, substituted or unsubstituted C$_{3-24}$-heteroaryl, or iv. are each independently selected from the group consisting of H, halogen, NO$_2$, CN, SO$_3$H, substituted or unsubstituted C$_{1-10}$-alkyl, substituted or unsubstituted C$_{2-10}$-alkenyl, substituted or unsubstituted C$_{2-10}$-alkynyl, substituted or unsubstituted C$_{4-10}$-alkeninyl, substituted or unsubstituted C$_{3-10}$-cycloalkyl, substituted or unsubstituted C$_{3-10}$-cycloalkenyl, substituted or unsubstituted C$_{5-10}$-cycloalkynyl, substituted or unsubstituted C$_{5-10}$-cycloalkeninyl, substituted or unsubstituted C$_{1-10}$-heteroalkyl, substituted or unsubstituted C$_{2-10}$-heteroalkenyl, substituted or unsubstituted C$_{2-10}$-heteroalkynyl, substituted or unsubstituted C$_{4-10}$-heteroalkeninyl, substituted or unsubstituted C$_{5-12}$-aryl, substituted or unsubstituted C$_{3-12}$-heteroaryl, or v. are all H, b) R$_A$ and R$_B$ are different and i. are each independently a substituted or unsubstituted cyclic, acyclic, linear or branched C$_{1-20}$-aliphatic radical or C$_{1-20}$-heteroaliphatic radical, or a substituted or unsubstituted C$_{5-20}$-aromatic radical or C$_{3-20}$-heteroaromatic radical, or ii. are each independently H, a substituted or unsubstituted cyclic, acyclic, linear or branched C$_{1-10}$-aliphatic radical or C$_{1-10}$-heteroaliphatic radical, or a substituted or unsubstituted C$_{5-12}$-aromatic radical or C$_{3-12}$-heteroaromatic radical, or iii. are each independently selected from the group consisting of substituted or unsubstituted C$_{1-20}$-alkyl, substituted or unsubstituted C$_{2-20}$-alkenyl, substituted or unsubstituted C$_{2-20}$-alkynyl, substituted or unsubstituted C$_{4-20}$-alkeninyl, substituted or unsubstituted C$_{3-20}$-cycloalkyl, substituted or unsubstituted C$_{3-20}$-cycloalkenyl, substituted or unsubstituted C$_{5-20}$-cycloalkynyl, substituted or unsubstituted C$_{5-20}$-cycloalkeninyl, substituted or unsubstituted C$_{1-20}$-heteroalkyl, substituted or unsubstituted C$_{2-20}$-heteroalkenyl, substituted or unsubstituted C$_{2-20}$-heteroalkynyl, substituted or unsubstituted C$_{4-20}$-heteroalkeninyl, substituted or unsubstituted C$_{5-24}$-aryl, substituted or unsubstituted C$_{3-24}$-heteroaryl, c) R$^{10}$ i. is a substituted or unsubstituted cyclic, acyclic, linear or branched C$_{1-20}$-aliphatic radical or C$_{1-20}$-heteroaliphatic radical, or a substituted or unsubstituted C$_{5-20}$-aromatic radical or C$_{3-20}$-heteroaromatic radical, or ii. is a substituted or unsubstituted cyclic, acyclic, linear or branched C$_{1-10}$-aliphatic radical or C$_{1-10}$-heteroaliphatic radical, or a substituted or unsubstituted C$_{5-12}$-aromatic radical or C$_{3-12}$-heteroaromatic radical, or iii. is a C$_{1-20}$-alkyl or C$_{2-20}$-alkenyl or a sugar radical, and d) R$^{12}$, R$^{13}$, R$^{14}$ and R$^{15}$ i. are each independently H, a substituted or unsubstituted cyclic, acyclic, linear or branched C$_{1-20}$-aliphatic radical or C$_{1-20}$-heteroaliphatic radical, a substituted or unsubstituted C$_{5-20}$-aromatic radical or C$_{3-20}$-heteroaromatic radical, and/or an electron acceptor, or ii. are each independently H, a substituted or unsubstituted cyclic, acyclic, linear or branched C$_{1-10}$-aliphatic radical or C$_{1-10}$-heteroaliphatic radical, or a substituted or unsubstituted C$_{5-12}$-aromatic radical or C$_{3-12}$-heteroaromatic radical, or iii. are each independently selected from the group consisting of H, substituted or unsubstituted C$_{1-20}$-alkyl, substituted or unsubstituted C$_{2-20}$-alkenyl, substituted or unsubstituted C$_{2-20}$-alkynyl, substituted or unsubstituted C$_{4-20}$-alkeninyl, substituted or unsubstituted C$_{3-20}$-cycloalkyl, substituted or unsubstituted C$_{3-20}$-cycloalkenyl, substituted or unsubstituted C$_{5-20}$-cycloalkynyl, substituted or unsubstituted C$_{5-20}$-cycloalkeninyl, substituted or unsubstituted C$_{1-20}$-heteroalkyl, substituted or unsubstituted C$_{2-20}$-heteroalkenyl, substituted or unsubstituted C$_{2-20}$-heteroalkynyl, substituted or unsubstituted C$_{4-20}$-heteroalkeninyl, substituted or unsubstituted C$_{5-24}$-aryl, substituted or unsubstituted C$_{3-24}$-heteroaryl, or iv. are each independently selected from the group consisting of H, substituted or unsubstituted C$_{1-10}$-alkyl, substituted or unsubstituted C$_{2-10}$-alkenyl, substituted or unsubstituted C$_{2-10}$-alkynyl, substituted or unsubstituted C$_{4-10}$-alkeninyl, substituted or unsubstituted C$_{3-10}$-cycloalkyl, substituted or unsubstituted C$_{3-10}$-cycloalkenyl, substituted or unsubstituted C$_{5-10}$-cycloalkynyl, substituted or unsubstituted C$_{5-10}$-cycloalkeninyl, substituted or unsubstituted C$_{1-10}$-heteroalkyl, substituted or unsubstituted C$_{2-10}$-heteroalkenyl, substituted or unsubstituted C$_{2-10}$-heteroalkynyl, substituted or unsubstituted C$_{4-10}$-heteroalkeninyl, substituted or unsubstituted C$_{5-12}$-aryl, substituted or unsubstituted C$_{3-12}$-heteroaryl, or v. are all H, or vi. are an electron acceptor or H, providing that R$^{12}$ and R$^{14}$ are each H and R$^{13}$ and R$^{15}$ are each an electron acceptor, or R$^{13}$ and R$^{15}$ are each H and R$^{12}$ and R$^{14}$ are each an electron acceptor.

3. The compound according to claim 1, wherein compound I is a compound according to the following formula Id

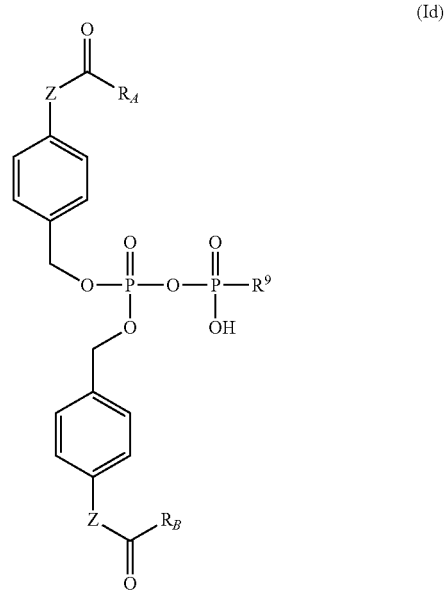

(Id)

or is a pharmaceutically acceptable salt thereof, and wherein Z=O, S or HN.

4. A medicinal product comprising as active ingredient a compound according to claim 1.

5. An antiviral medicinal product comprising as active ingredient a compound according to claim 1.

6. A pharmaceutical composition, comprising a compound according to claim 1 and a pharmaceutically acceptable carrier.

7. A method for producing a compound having general formula I

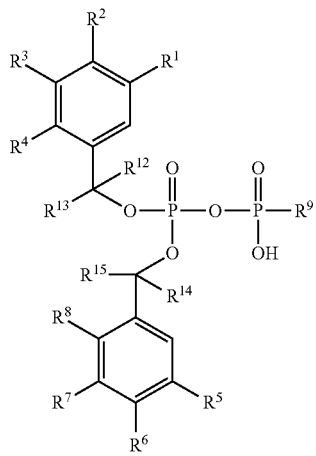

(I)

or a pharmaceutically acceptable salt thereof, wherein $R^1$, $R^3$, $R^5$ and $R^7$ are independently H, halogen, $NO_2$, CN, $SO_3H$, a substituted or unsubstituted cyclic, acyclic, linear or branched aliphatic or heteroaliphatic radical, or a substituted or unsubstituted aromatic or heteroaromatic radical, $R^2$ and $R^4$ are independently H or Z—C(Y)—$R_A$, but are not both H, $R^6$ and $R^8$ are independently H, Z—C(Y)—$R_B$, but are not both H, Z, Y is independently O, S or HN, $R_A$ and $R_B$ are different and each is a substituted or unsubstituted cyclic, acyclic, linear or branched aliphatic or heteroaliphatic radical, or a substituted or unsubstituted aromatic or heteroaromatic radical, $R^9$ is nucleoside, nucleoside monophosphate, nucleoside analogue, nucleoside monophosphate analogue, O—$R^{10}$, OP(O)(OH)-$R^{10}$ or OP(O)(OH) —O—$R^{10}$, wherein $R^{10}$ is a substituted or unsubstituted cyclic, acyclic, linear or branched aliphatic or heteroaliphatic radical, or a substituted or unsubstituted aromatic or heteroaromatic radical, and wherein $R^{12}$, $R^{13}$, $R^{14}$ and $^{15}$ are independently H, a substituted or unsubstituted cyclic, acyclic, linear or branched aliphatic or heteroaliphatic radical, a substituted or unsubstituted aromatic or heteroaromatic radical, and/or an electron acceptor, comprising the following steps:

$a_1$) reacting a compound having general formula II$_A$

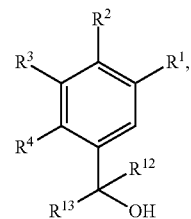

(II$_A$)

wherein $R^1$, $R^2$, $R^3$, $R^4$, $R^{12}$ and $R^{13}$ are defined as above, with i) phosphorus trichloride $PCl_3$ and N,N-diisopropylamine, or ii) bis(N,N-diisopropylamino)chlorophosphine to synthesise a compound having general formula III

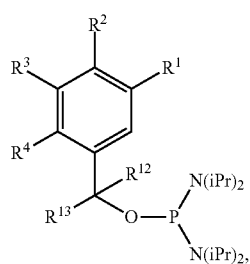

(III)

$b_1$) reacting the compound having formula III obtained in a) with a compound having general formula II$_B$

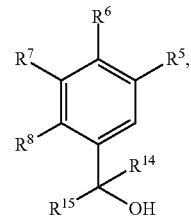

(II$_B$)

wherein $R^5$, $R^6$, $R^7$, $R^8$, $R^{14}$ and $R^{15}$ are defined as above, to synthesise a compound having general formula IV

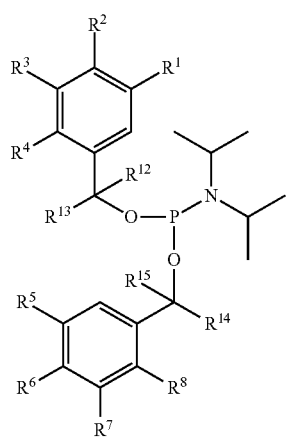

(IV)

c₁) reacting the compound having formula IV obtained in b) to react with a compound according to general formula V

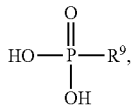

(V)

wherein R⁹ is defined as above, or a₂) reacting a compound having general formula II_A

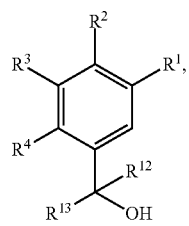

(II_A)

wherein R¹, R², R³, R⁴, R¹², and R¹³ are defined as above, with diphenylphosphonate to synthesise a compound having general VI

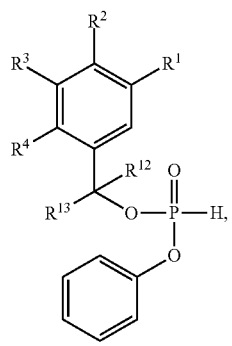

(VI)

b₂) reacting the compound with formula VI obtained in a) with a compound having general formula II_B

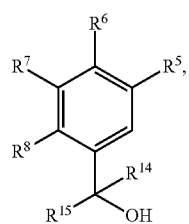

(II_B)

wherein R⁵, R⁶, R⁷, R⁸, R¹⁴ and R¹⁵ are defined as above, to synthesise a compound having general formula VII

(VII)

c₂) reacting the compound with formula VII obtained in b) with i) a compound according to general formula V $$HO-\overset{\overset{O}{\|}}{\underset{OH}{P}}-R^9,$$ (V)

or ii) with phosphoric acid or a phosphoric acid salt and R⁹ or a compound comprising R⁹, wherein R⁹ is defined as above.

8. The method according to claim 7, wherein
a) R¹, R³, R⁵ and R⁷
   i. are each independently H, halogen, NO₂, CN, SO₃H, a substituted or unsubstituted cyclic, acyclic, linear or branched C₁₋₂₀-aliphatic radical or C₁₋₂₀-heteroaliphatic radical, or a substituted or unsubstituted C₅₋₂₀-aromatic radical or C₃₋₂₀-heteroaromatic radical, or
   ii. are each independently H, halogen, NO₂, CN, SO₃H, a substituted or unsubstituted cyclic, acyclic, linear or branched C₁₋₁₀-aliphatic radical or C₁₋₁₀-heteroaliphatic radical, or a substituted or unsubstituted C₅₋₁₂-aromatic radical or C₃₋₁₂-heteroaromatic radical, or
   iii. are each independently selected from the group consisting of H, halogen, NO₂, CN, SO₃H, substituted or unsubstituted C₁₋₂₀-alkyl, substituted or unsubstituted C₂₋₂₀-alkenyl, substituted or unsubstituted C₂₋₂₀-alkynyl, substituted or unsubstituted C₄₋₂₀-alkeninyl, substituted or unsubstituted C₃₋₂₀-cycloalkyl, substituted or unsubstituted C₃₋₂₀-cycloalkenyl, substituted or unsubstituted C₅₋₂₀-cycloalkynyl, substituted or unsubstituted C₅₋₂₀-cycloalkeninyl, substituted or unsubstituted C₁₋₂₀-heteroalkyl, substituted or unsubstituted C₂₋₂₀-heteroalkenyl, substituted or unsubstituted C₂₋₂₀-heteroalkynyl, substituted or unsubstituted C₄₋₂₀-heteroalkeninyl, substituted or unsubstituted C₅₋₂₄-aryl, substituted or unsubstituted C₃₋₂₄-heteroaryl, or
   iv. are each independently selected from the group consisting of H, halogen, NO₂, CN, SO₃H, substituted or unsubstituted C₁₋₁₀-alkyl, substituted or unsubstituted C₂₋₁₀-alkenyl, substituted or unsubstituted C₂₋₁₀-alkynyl, substituted or unsubstituted C₄₋₁₀-alkeninyl, substituted or unsubstituted C₃₋₁₀-cycloalkyl, substituted or unsubstituted C₃₋₁₀-cycloalkenyl, substituted or unsubstituted C₅₋₁₀-cycloalkynyl, substituted or unsubstituted $C_{5-10}$-cycloalkeninyl, substituted or unsubstituted $C_{1-10}$-heteroalkyl, substituted or unsubstituted $C_{2-10}$-heteroalkenyl, substituted or unsubstituted $C_{2-10}$-heteroalkynyl, substituted or unsubstituted $C_{4-10}$-heteroalkeninyl, substituted or unsubstituted $C_{5-12}$-aryl, substituted or unsubstituted $C_{3-12}$-heteroaryl, or v. are all H, b) $R_A$ and $R_B$ are different and i. are each independently a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, or ii. are each independently H, a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, or iii. are each independently selected from the group consisting of substituted or unsubstituted $C_{1-20}$-alkyl, substituted or unsubstituted $C_{2-20}$-alkenyl, substituted or unsubstituted $C_{2-20}$-alkynyl substituted or unsubstituted $C_{4-20}$-alkeninyl, substituted or unsubstituted $C_{3-20}$-cycloalkyl, substituted or unsubstituted $C_{3-20}$-cycloalkenyl, substituted or unsubstituted $C_{5-20}$-cycloalkynyl substituted or unsubstituted $C_{5-20}$-cycloalkeninyl, substituted or unsubstituted $C_{1-20}$-heteroalkyl, substituted or unsubstituted $C_{2-20}$-heteroalkenyl, substituted or unsubstituted $C_{2-20}$-heteroalkynyl, substituted or unsubstituted $C_{4-20}$-heteroalkeninyl, substituted or unsubstituted $C_{5-24}$-aryl, substituted or unsubstituted $C_{3-24}$-heteroaryl, c) $R^{10}$ i. is a substituted or unsubstituted cyclic, acyclic, linear or branched $C_{1-20}$-aliphatic radical or $C_{1-20}$-heteroaliphatic radical, or a substituted or unsubstituted $C_{5-20}$-aromatic radical or $C_{3-20}$-heteroaromatic radical, or ii. is a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, or iii. is a $C_{1-20}$-alkyl or $C_{2-20}$-alkenyl or a sugar radical, and d) $R^{12}, R^{13}, R^{14}$ and $R^{15}$ i. are each independently H, a substituted or unsubstituted cyclic, acyclic, linear or branched $C_{1-20}$-aliphatic radical or $C_{1-20}$-heteroaliphatic radical, a substituted or unsubstituted $C_{5-20}$-aromatic radical or $C_{3-20}$-heteroaromatic radical, and/or an electron acceptor, or ii. are each independently H, a substituted or unsubstituted cyclic, acyclic, linear or branched $C_{1-10}$-aliphatic radical or $C_{1-10}$-heteroaliphatic radical, or a substituted or unsubstituted $C_{5-12}$-aromatic radical or $C_{3-12}$-heteroaromatic radical, or iii. are each independently selected from the group consisting of H, substituted or unsubstituted $C_{1-20}$-alkyl, substituted or unsubstituted $C_{2-20}$-alkenyl, substituted or unsubstituted $C_{2-20}$-alkynyl substituted or unsubstituted $C_{4-20}$-alkeninyl, substituted or unsubstituted $C_{3-20}$-cycloalkyl, substituted or unsubstituted $C_{3-20}$-cycloalkenyl, substituted or unsubstituted $C_{5-20}$-cycloalkynyl substituted or unsubstituted $C_{5-20}$-cycloalkeninyl, substituted or unsubstituted $C_{1-20}$-heteroalkyl, substituted or unsubstituted $C_{2-20}$-heteroalkenyl, substituted or unsubstituted $C_{2-20}$-heteroalkynyl, substituted or unsubstituted $C_{4-20}$-heteroalkeninyl, substituted or unsubstituted $C_{5-24}$-aryl, substituted or unsubstituted $C_{3-24}$-heteroaryl, or iv. are each independently selected from the group consisting of H, substituted or unsubstituted $C_{1-10}$-alkyl, substituted or unsubstituted $C_{2-10}$-alkenyl, substituted or unsubstituted $C_{2-10}$-alkynyl, substituted or unsubstituted $C_{4-10}$-alkeninyl, substituted or unsubstituted $C_{3-10}$-cycloalkyl, substituted or unsubstituted $C_{3-10}$-cycloalkenyl, substituted or unsubstituted $C_{5-10}$-cycloalkynyl, substituted or unsubstituted $C_{5-10}$-cycloalkeninyl, substituted or unsubstituted $C_{1-10}$-heteroalkyl, substituted or unsubstituted $C_{2-10}$-heteroalkenyl, substituted or unsubstituted $C_{2-10}$-heteroalkynyl, substituted or unsubstituted $C_{4-10}$-heteroalkeninyl, substituted or unsubstituted $C_{5-12}$-aryl, substituted or unsubstituted $C_{3-12}$-heteroaryl, or v. are all H, or vi. are an electron acceptor or H, providing that $R^{12}$ and $R^{14}$ are each H and $R^{13}$ and $R^{15}$ are each an electron acceptor, or $R^{13}$ and $R^{15}$ are each H and $R^{12}$ and $R^{14}$ are each an electron acceptor.

9. An antiretroviral medicinal product comprising as active ingredient a compound according to claim 1.

10. The antiretroviral medicinal product according to claim 9, wherein the medicinal product is for the treatment of an HIV-infection, hepatitis-infection, influenza or haemorrhagic fever.

11. The compound according to claim 2, wherein $R_A$ and $R_B$ are different and are each independently selected from the group consisting of $C_{1-20}$-alkyl or $C_{2-20}$-alkenyl.

12. The method according to claim 8, wherein $R_A$ and $R_B$ are different and are each independently selected from the group consisting of $C_{1-20}$-alkyl or $C_{2-20}$-alkenyl.

13. The compound according to claim 3, wherein $Z = O$.

* * * * *